US008415449B2

(12) United States Patent
Kohn et al.

(10) Patent No.: US 8,415,449 B2
(45) Date of Patent: Apr. 9, 2013

(54) BIORESORBABLE POLYMERS SYNTHESIZED FROM MONOMER ANALOGS OF NATURAL METABOLITES

(75) Inventors: Joachim B. Kohn, Piscataway, NJ (US); Durgadas Bolikal, Edison, NJ (US); Ramiro Rojas, Stockholm (SE)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/387,798

(22) PCT Filed: Jul. 31, 2010

(86) PCT No.: PCT/US2010/044049

§ 371 (c)(1),
(2), (4) Date: Apr. 16, 2012

(87) PCT Pub. No.: WO2011/014858

PCT Pub. Date: Feb. 3, 2011

(65) Prior Publication Data

US 2012/0197001 A1 Aug. 2, 2012

Related U.S. Application Data

(60) Provisional application No. 61/230,558, filed on Jul. 31, 2009.

(51) Int. Cl.
*C08G 64/00* (2006.01)
*C08G 63/02* (2006.01)

(52) U.S. Cl.
USPC ............................ 528/203; 525/433; 528/202

(58) Field of Classification Search .................. 525/433; 528/202, 203
See application file for complete search history.

(56) References Cited

U.S. PATENT DOCUMENTS

| | | | |
|---|---|---|---|
| 3,636,956 | A | 1/1972 | Schneider |
| 4,744,365 | A | 5/1988 | Kaplan et al. |
| 4,747,956 | A | 5/1988 | Kiniwa |
| 4,822,829 | A | 4/1989 | Muller et al. |
| 5,066,772 | A | 11/1991 | Tang et al. |
| 5,702,717 | A | 12/1997 | Cha et al. |
| 6,120,491 | A | 9/2000 | Kohn et al. |
| 6,228,969 | B1 | 5/2001 | Lee et al. |
| 6,355,754 | B1 | 3/2002 | Olson et al. |
| 6,475,477 | B1 | 11/2002 | Kohn et al. |
| 6,943,214 | B2 | 9/2005 | Flexman |
| 7,169,187 | B2 | 1/2007 | Datta et al. |
| 2006/0024266 | A1 | 2/2006 | Brandom et al. |
| 2006/0034891 | A1 | 2/2006 | Lawin et al. |
| 2007/0231365 | A1 | 10/2007 | Wang et al. |
| 2008/0063685 | A1 | 3/2008 | Wang et al. |
| 2008/0112999 | A1 | 5/2008 | Baluca |
| 2008/0146504 | A1 | 6/2008 | Bonnin |
| 2008/0152690 | A1 | 6/2008 | Kohn et al. |
| 2008/0187567 | A1 | 8/2008 | Kohn et al. |

OTHER PUBLICATIONS

Sousa, A., et al., "Selective Protein Adsorption on a Phase-Separated Solvent-Cast Polymer Blend", Langmuir, 22, 2006, pp. 6286-6292.
Tangpasuthadol, V., et al., "Thermal properties and physical ageing behaviour of tyrosine-derived polycarbonates", Biomaterials, 1996, vol. 17, No. 4., pp. 463-468.
Sakar, D., et al., Structure-Property Relationship of L-Tyrosine-Based Polyurethanes for Biomaterial Applications, Journal of Applied Polymer Science, vol. 108, 23435-2355 (2008).
Polycarprolactone diol, 2011 obtained from the Sigma-Aldrich website: (http://www.sigmaaldrich.com/catalog/ProductDetail.do?D7=0&N5=SEARCH_CONCAT_PNO%7CBRAND_KEY&N4=189421%7CALDRICH&N25=0&QS=ON&F=SPEC).
Dobrzynski et al. Structure-Property Relationships of Copolymers Obtained by Ring-Opening Polymerization of Glycolide and e-Caprolactone. Part 1. Synthesis and Characterization. Biomacromolecules 6(1): 483-488. 2005.

*Primary Examiner* — Terressa Boykin
(74) *Attorney, Agent, or Firm* — Fox Rothschild LLP

(57) ABSTRACT

This invention discloses biocompatible polymers prepared from monomers (IV), and (IVa), or derivatives thereof, for which the variables are described in the claims and specification. These polymers may be bioresorbable and thus useful for manufacture of medical devices. Therefore, methods for preparing these polymers and medical devices prepared therefrom are also encompassed by this disclosure.

(IV)

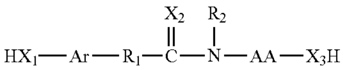

(IVa)

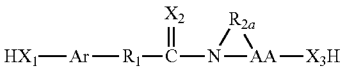

22 Claims, No Drawings

BIORESORBABLE POLYMERS SYNTHESIZED FROM MONOMER ANALOGS OF NATURAL METABOLITES

CROSS-REFERENCE TO RELATED APPLICATIONS

This application is the U.S. National Phase of International Patent Application Serial No. PCT/US10/44049, filed on Jul. 31, 2010, which claims priority under 35 U.S.C. §119(e) to U.S. Provisional Patent Application Ser. No. 61/230,558, filed on Jul. 31, 2009, both of which are hereby incorporated by reference in their entireties for all purposes.

STATEMENT REGARDING FEDERALLY SPONSORED RESEARCH

The invention described herein was supported in whole or in part by grants from the National Institutes of Health (Grant No. EB001046). The U.S. Government has certain rights in this invention.

FIELD OF THE INVENTION

The present invention relates to new bioresorbable polymers synthesized from monomer analogs of natural metabolites. In particular, the present invention relates to co-polymers synthesized from novel monomers and analogs of amino acids that contribute advantageous synthesis, processing and material properties to the polymers prepared therefrom, including particularly advantageous degradation profiles.

BACKGROUND OF THE INVENTION

U.S. Pat. No. 5,099,060 discloses diphenolic monomers based on 3-(4-hydroxy-phenyl)propionic acid and L-tyrosine alkyl esters (desaminotyrosyl-tyrosine alkyl esters). Subsequent related patents involve variations of this basic monomer structure, including halogenated radiopaque diphenolic monomers, such as the 3,5-di-iododesaminotyrosyl-tyrosine esters ($I_2$DTR, wherein R is an alkyl group, e.g., E=ethyl, H=hexyl, O=octyl, etc.) disclosed by U.S. Patent Application Publication No. 20060034769. The disclosures of both publications are incorporated herein by reference. These monomers, although useful in many applications, have several limitations as explained below.

In the context of these teachings, the term "degradation" is defined as the process leading to the chemical cleavage of the polymer backbone, resulting in a reduction in polymer molecular weight and mechanical strength. The rate of polymer degradation under physiological conditions is predominantly determined by the type of bonds used to link the individual polymer repeat units together. Hence, polyanhydrides, e.g., polymers containing the highly labile anhydride linkage, will tend to degrade faster than polyesters. In contrast, the term "resorption" is defined as the process leading to a reduction of the mass of an implanted device. The rate of resorption is predominantly governed by the solubility of the polymer itself or its degradation products. The resorption of an implant is complete, once the entire mass of the implant has been removed from the implant site. Degradation and resorption do not always go hand-in-hand. Just for the purpose of providing an illustrative example, a sugar cube in water will "resorb" (e.g., loose mass and ultimately disappear) without any chemical degradation process. Likewise, comparing the degradation and resorption profiles of two different polyanhydrides, one can expect that both polymers will degrade when exposed to aqueous media, but the polymer degrading into more soluble degradation products will be losing mass faster and will, therefore, be the polymer that will resorb faster when implanted in a patient.

The monomers provided in the above mentioned patent applications have two phenolic hydroxyl groups, limiting the resulting homopolymers to fully aromatic backbone structures. Such polymers have generally good mechanical properties—but slow degradation rates. Moreover, when the monomers are sparingly soluble in water, the degradation products formed during polymer degradation are often also sparingly soluble in water. This property can prevent the degrading polymer from being resorbed at a time scale that is concomitant with polymer degradation. Hence, such polymers will have some use limitations as medical implant materials when the processes of degradation and resorption need to occur concomitantly. The previously described homopolymers prepared from the previously described sparingly-soluble monomers will not have any significant weight loss while the degradation of the homopolymer backbone results in reduction in the polymer molecular weight and loss of mechanical strength. As a result implantable medical devices and drug delivery implants prepared from the previously described homopolymers that are intended to be resorbed are still substantially undissolved at the end of their useful life as measured by reduction in polymer molecular weight or mechanical strength.

This is particularly a problem for drug delivery implants and implantable medical devices that are intended to be replaced as part of a long-term treatment regimen. For example, a polymeric implant for the delivery of birth control hormones is intended to be replaced at the terminal stage of polymer degradation when essentially all of the hormones have been released as a consequence of polymer backbone degradation and mass loss. However, implants formed with many of the previously described homopolymers will not only be substantially undissolved when a replacement device must be implanted, significant mass will remain when the next replacement device is due for implantation. This creates the untenable situation where patients would be expected to endure having several depleted polymeric drug delivery implants in their body at various stages of resorption while replacement devices continue to be implanted at a periodic rate.

Homopolymers of non-aromatic amino acids have been prepared. Examples are polyglycine, polyalanine, polyserine, polyleucine. However, despite their apparent potential as biomaterials, such poly(amino acids) have actually found few practical applications. A major problem is that most of the poly(amino acids) are highly intractable (e.g., non-processable by conventional thermal or solvent fabrication methods), which limits their utility.

The elegant synthesis of a copolymer derived from lactic acid and lysine was reported by Barrera et al., Macromol., (28), 425-432 (1995). The lysine residue was utilized to chemically attach a cell-adhesion promoting peptide to the copolymer.

Other polymers of amino acids and hydroxy acids are disclosed by U.S. Pat. No. 3,773,737. The non-aromatic copolymers were random copolymers prepared from cyclic monomers by ring-opening polymerization. The composition of the copolymers is highly dependent on the relative reactivity of the two types of cyclic monomers and on the exact polymerization conditions used. It is hard to control the composition and hard to predict the polymer properties. Also, there may be large batch-to-batch variations in the polymer microstructure and sequence. Further, most previous reports only described polymers of low molecular weight ($M_w$<10,000).

There are very few degradable polymers for medical uses that have been successfully commercialized. Poly(glycolic acid) (PGA), poly(lactic acid) (PLA) and their copolymers are representative examples. However, these polymers degrade to form tissue-irritating acids. Polymers of tyrosine and hydroxy acids such as glycolic acid and lactic acid have also been prepared and are disclosed by U.S. Pat. No. 6,284,862. There still remains a need for bioresorbable polymers suitable for use as tissue-compatible materials.

For example, many investigators in the emerging field of tissue engineering have proposed to engineer new tissues by transplanting isolated cell populations on biomaterial scaffolds to create functional new tissues in vivo. Bioresorbable materials whose degradation and resorption rates can be tailored to correspond to the rate of tissue growth are needed. It is desirable that libraries of many different materials be available so that the specific polymer properties can be optimally matched with the requirements of the specific application under development.

SUMMARY OF THE INVENTION

This need is met by preferred embodiments of the present invention. Embodiments of the present invention provide novel classes of aliphatic-aromatic monomers and bioresorbable polymers derived therefrom that hydrolytically degrade under physiological conditions. The monomers are dipeptides of tyrosine analogs and amino acids with substituent groups through which the dipeptide monomer can be polymerized. Monomer solubility and the mechanical properties of the polymer can be varied by selection of the amino acid which is incorporated into the dipeptide monomer.

The present invention provides polymers comprising a repeating unit having a structure selected from Formula (I) and Formula (Ia):

(I)

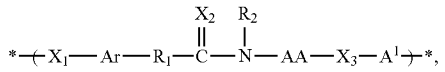

(II)

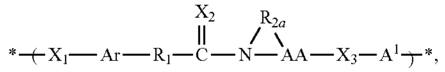

for which the variables are defined as follows:

Ar is a phenyl ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA- define a heterocyclic ring;

$R_3$ is selected from the group consisting of hydrogen and alkyl groups containing from 1 to 30 carbon atoms;

AA has a pendant $COOR_4$ group wherein $R_4$ is selected from the group consisting of hydrogen, alkyl, heteroalkyl and alkylaryl groups containing up to 30 carbon atoms and alkyl-terminated poly(alkylene oxide) groups of molecular weight 100 to 10,000;

AA and $X_3$H of Formula I are selected so that ($R_2$—HN—) AA-$X_3$H defines an —$X_3$H substituted amino acid and AA and $X_3$H of Formula Ia are selected so that

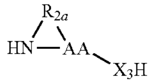

defines an $X_3$H— substituted amino acid;

$A^1$ at each occurrence is independently selected from:

a bond,

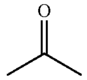, 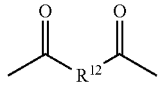, 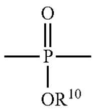, 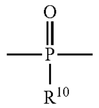, and 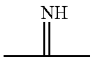;

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl.

In one aspect, the polymer of the present invention has a glass transition temperature or crystalline melting temperature greater than 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of at least about 3 mg/mL.

In another aspect, the polymer of the present invention has a glass transition temperature or crystalline melting temperature greater than 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of less than about 3 mg/mL.

In another aspect, the polymer of the present invention has a glass transition temperature or crystalline melting temperature less than about 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. greater than about 3 mg/mL.

In another aspect, the polymer of the present invention has a glass transition temperature or crystalline melting temperature less than about 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of less than about 3 mg/mL.

Alkyl, heteroalkyl, alkenyl and heteroalkenyl groups are straight-chained or branched. The heteroalkyl and heteroalkenyl groups contain from one to eight heteroatoms. Heteroatoms are independently selected from O, S and N-methyl. Examples of alkyl-terminated poly(alkylene oxides) include methoxy-terminated poly(ethylene glycols) (PEG) of molecular weight 400 to 4,000, methoxy-terminated poly (propylene glycols) (PPG), and methoxy-terminated block copolymers of PEG and PPG.

Aromatic rings may be substituted with from 1 to 4 of the identified groups as long as the substitution patterns are chemically feasible. Any combination of substituents containing more than two nitro groups is potentially explosive and expressly excluded from these teachings.

Polymers that include repeating units of Formula I and/or Formula Ia may be referred to herein as "polymers of Formula I and Formula Ia" or "Formula I and Ia polymers." Polymers of Formula I and Formula Ia include polymers containing either or both Formula I and Formula Ia repeating units. Other repeating units may be present, including repeating units derived from desaminotyrosyl-tyrosine, including the monomers disclosed by U.S. Pat. No. 5,099,060.

In another aspect the present invention provides copolymers comprising repeating unit of formula (I) and Formula I and/or Formula Ia polymers wherein AA and $X_3$ are selected so that ($R_2$—HN—)AA-$X_3$H and

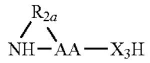

define an alpha-amino acid wherein ($R_2$—HN—)AA-$X_3$H is optionally N-alkyl substituted. In a more specific embodiment, the alpha amino acid is a naturally-occurring amino acid. Alpha-amino acids from which the polymers of the present invention may be prepared include, but are not limited to, cysteine, threonine, serine, lysine, thyronine, thyroxine, hydroxy-proline, mercapto-proline, hydroxy-leucine, mercapto-leucine, hydroxy-isoleucine, mercapto-isoleucine, hydroxy-tryptophan, mercapto-tryptophan, mercapto-alanine, mercapto-valine and mercapto-phenylalanine.

Included among the polymer embodiments of the Formula I and Formula Ia are four distinct polymer embodiments. According to the first polymer embodiment, AA and $X_3$ are selected so that the degradation products of polymers of Formula I and Formula Ia resorb more quickly under physiological conditions than comparable polymers of desaminotyrosyl-tyrosine alkyl esters and the polymers have intrinsic physical properties suitable for use in load-bearing medical implants such as vascular or coronary stents.

For purposes of the present invention, "physiological conditions" are defined as storage in phosphate buffered saline solution (PBS), 0.1 M, pH 7.4 at 37° C., and polymers that resorb more quickly are defined as containing at least 10 mol % of monomers comprising either the Formula I or Formula Ia repeating units having a PBS solubility under physiological conditions of at least about 3 mg/mL and preferably at least about 5 mg/mL to provide the desired rate of resorption. The monomer comprising either Formula I or Formula Ia repeating units may contain other moieties or substituents, provided that the requisite degree of PBS solubility is conserved. All of this is readily determined by one of ordinary skill in the art without undue experimentation. Embodiments according to the present invention include polymers containing up 90 mol % of said monomer and polymers consisting entirely of said monomers. Other monomers and repeating units may be used to design polymers with a desirable rate of resorption.

"Load-bearing medical implants" are defined as implantable medical devices that are required by their intended use to withstand forces caused by compression, bending, or stretching of the implant. Because of the significant variations in shape, size, and use of load-bearing medical implants, the physicomechanical properties of polymers suitable for load-bearing implants cannot be described in general terms, except for the following requirements: As a general rule, load-bearing medical implants can only be fabricated from (i) amorphous polymers that have a glass transition temperature greater than 37° C. when fully hydrated under physiological conditions and, (ii) from crystalline polymers that have a crystalline melting temperature greater than 37° C. when fully hydrated under physiological conditions. In addition, the equilibrium water content when fully hydrated under physiological conditions is typically less than 20 wt %, preferably less than 10 wt % and more preferably less than 5 wt %. These required polymer properties can be achieved by carefully optimizing the chemical composition of the polymer backbone structure, including Formula I repeating units, Formula Ia repeating units, other repeating units, and combinations thereof.

Examples of Formula I and Formula Ia polymers according to the first polymer embodiment include, but are not limited to, polymers in which AA and $X_3$ of Formula I are selected so that ($R_2$—HN—)AA-$X_3$H defines an amino acid selected from serine, threonine, hydroxylysine, cysteine, and AA and $X_3$ of Formula Ia are selected so that:

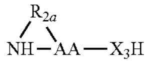

defines an amino acid selected from cis-hydroxy-proline, trans-hydroxy-proline, cis-mercapto-proline and trans-mercapto-proline.

According to the second polymer embodiment of the invention, AA and $X_3$ are selected so that the degradation products of the polymers of Formula I and Formula Ia do not necessarily resorb significantly more quickly under physiological conditions than comparable polymers of desaminotyrosyl-tyrosine alkyl esters. That is, they resorb at about the same rate or slower. However, polymers according to this embodiment still have intrinsic physical properties suitable for use in load-bearing medical implants.

Polymers according to this embodiment are defined as containing at least 10 mol % of monomers comprising either Formula I or Formula Ia repeating units having a PBS solubility under physiological conditions of less than about 3 mg/mL to provide the desired slow rate of resorption, and having the requisite glass transition or crystalline melting temperature and equilibrium water content for the desired load-bearing intrinsic physical properties. Examples of polymers according to the second polymer embodiment include, but are not limited to, polymers in which AA and $X_3$ of Formula I are selected so that ($R_2$—HN—)AA-$X_3$H defines an amino acid selected from mercapto-phenylalanine, thryronine and thyroxine.

According to a third polymer embodiment of the invention, AA and $X_3$ are selected so that the degradation products of the polymers of Formula I and Formula Ia do not necessarily resorb significantly more quickly under physiological conditions than comparable polymers of desaminotyrosyl-tyrosine alkyl esters and the polymers do not have intrinsic physical properties suitable for use in load-bearing medical implants. Polymers according to this embodiment have utility in other uses for biocompatible polymers, such as drug delivery implants, bridging materials, tissue sealants, adhesion prevention materials, tissue scaffolds where rigidity is not essential, and the like.

Polymers lacking intrinsic physical properties suitable for use in load-bearing medical implants include, if the polymer is amorphous, a glass transition temperature less than 37° C. when fully hydrated under physiological conditions and, if the polymer is crystalline, a crystal-line melting temperature less than 37° C. when fully hydrated under physiological conditions. In addition, the equilibrium water content when fully hydrated under physiological conditions is typically greater than 20 wt %.

Polymers according to this embodiment are defined as being polymerized from at least 10 mol % of monomers that comprising either Formula I or Formula Ia repeating units having a PBS solubility under physiological conditions effective to provide the desired rate of resorption, and have the requisite glass transition or crystalline melting temperature and equilibrium water content for the desired intrinsic physical properties. Polymers according to this embodiment of the invention include, but are not limited to, polymers in which AA and $X_3$ of Formula I are selected so that ($R_2$—HN—)AA-$X_3$H defines an amino acid selected from hydroxy-leucine, mercapto-leucine, hydroxy-isoleucine, mercapto-isoleucine and mercapto-valine.

According to a fourth polymer embodiment of the invention, AA and $X_3$ are selected so that the degradation products of polymers of Formula I and Formula Ia resorb more quickly under physiological conditions than comparable polymers of desaminotyrosyl-tyrosine alkyl esters and the polymers do not have intrinsic physical properties suitable for use in load-bearing medical implants. Polymers according to this embodiment are defined as being polymerized from at least 10 mol % of monomers comprising either Formula I or Formula Ia repeating units having a PBS solubility under physiological conditions to provide the desired rate of resorption, and having the requisite glass transition or crystalline melting temperature and equilibrium water content for the desired intrinsic physical properties. Examples of polymers according to this embodiment of the invention include, but are not limited to, polymers in which AA and $X_3$ of Formula I are selected so that ($R_2$—HN—)AA-$X_3$H defines an amino acid selected from cysteine, threonine, serine, lysine and mercapto-alanine.

Independent of each polymer embodiment, the same Formula I and/or Formula Ia repeating units can provide both the desired resorption properties and the intrinsic physical properties. In the alternative, one set of Formula I and/or Formula Ia repeating units are selected to provide the desired rate of resorption and combined with a second set of Formula I and/or Formula Ia repeating units selected to provide intrinsic physical properties. Additional repeating units can be present that also contribute to the desired degradation properties and intrinsic physical properties, including repeating units with pendant free carboxylic acid groups. The selection of appropriate repeating units for each polymer embodiment is readily determined by one of ordinary skill in the art without undue experimentation.

Independent of each polymer embodiment, the present invention provides polymers according to Formula I and Formula Ia in which $X_1$ and $X_2$ are 0, wherein the polymers are prepared from monomers that are dimers of a hydroxy-phenyloxy-, hydroxy-phenylamino- or hydroxy-phenylthioalkanoic or alkenoic acid and an amino acid.

More specifically, Formula I and Formula Ia polymers are provided independent of each embodiment that are formed from monomers that are dimers of a phenyoxyalkanoic acid, a phenylaminoalkanoic acid or a phenylthioalkanoic acid and an amino acid. The phenoxy-, phenylamino- and phenylthioalkanoic acids unexpectedly contribute useful physical properties to the Formula I and Ia polymers that are not obtained from polymers formed from monomers combining two or more amino acids. The advantageous physical properties in no particular order of importance include a lack of a chiral center, which does not give rise to diastereomers when coupled with amino acids. Also, because the COOH on is not linked to a chiral carbon, there is no racemization during coupling to make the monomer. Furthermore, the phenoxy-, phenylamino- and phenylthioalkanoic acids easier to iodinate than an aromatic amino acid such as tyrosine when a radio-opaque polymer is desired and the aromatic ring imparts good mechanical properties to polymers.

In another aspect the present invention provides co-polymers having at least two different repeating units, i.e., a repeating unit of formula (Ia) and a repeating unit of Formula I and/or Formula Ia, wherein in repeating unit of formula (II) $R_4$ is hydrogen, so that $COOR_4$ is a pendant free carboxylic acid group, and in repeating unit of formula (IIa) $R_4$ is an alkyl group containing up to 18 carbon atoms, so that $COOR_4$ is a pendant alkyl ester group. Among the copolymers provided are copolymers in which between about 1 and about 50% of the AA groups have pendant free carboxylic acid groups. Among other copolymers provided are copolymers in which greater than about 5% but less than about 33% of the AA groups have pendant free carboxylic acid groups.

Polymers with a sufficient number of aromatic rings sufficiently substituted with bromine or iodine are inherently radio-opaque. The present invention therefore also provides, independent of any particular polymer embodiment, polymers according to Formula I and Ia in which the aromatic rings are substituted with at least one iodine or bromine atom, on at least one and preferably on both ring positions ortho to $X_1$. In a more specific aspect of each embodiment, at least 50% of the Ar groups are substituted with from two to four iodine atoms, bromine atoms, or combinations thereof.

The present invention is thus based in part on the recognition that valuable polymers are obtained when the phenoxy-, phenylamino- and phenylthioalkanoic acids are kept constant and the monomer and polymer properties are modified by varying the amino acid coupled to the phenoxy-, phenylamino- and phenylthioalkanoic acids that otherwise would not be obtained if at the same time the phenoxy-, phenylamino- and phenylthioalkanoic acids were replaced by amino acids or other amino acid analogs. The new monomers, the resulting polymers, and their respective properties represent new and valuable biomaterials in addition to the desamino-tyrosyl-tyrosine alkyl ester monomers and the polymers polymerized therefrom disclosed before.

Polymers according to the present invention include polyethers, polyurethanes, polycarbamates, polythiocarbonates, polycarbonodithionates) and polythiocarbamates. Polycarbonates, specifically poly(amide carbonates), as well as polyurethanes, poly(carbamates), polythiocarbonates, polycarbonodithionates and polythiocarbamates are prepared by the process disclosed by U.S. Pat. No. 5,198,507, the disclosure of which is incorporated by reference. Polyesters, specifically poly(ester amides), are prepared by the process disclosed by U.S. Pat. No. 5,216,115, the disclosure of which is incorporated by reference. Polyiminocarbonates are prepared by the process disclosed by U.S. Pat. No. 4,980,449, the disclosure of which is incorporated by reference. Polyethers are prepared by the process disclosed by U.S. Pat. No. 6,602,497, the disclosure of which is incorporated by reference.

Independent of any particular polymer embodiment, the present invention also provides polymers that include a recurring unit according to Formula I, Formula Ia, Formula II and/or Formula IIa that are copolymerized with any number of other recurring units. For example the present invention provides polymers having a recurring unit according to Formula I, Formula Ia, Formula II and/or Formula IIa that are block co-polymerized with recurring poly(alkylene oxide) block units having a structure according to Formula III:

$$-\!\!\left(B-A^2\right)\!\!- \qquad \text{(III)}$$

wherein B is —O—((CHR$^6$)$_p$—O)$_q$—; each R$^6$ is independently H or $C_1$ to $C_3$ alkyl; p is an integer ranging between about one and about 4; q is an integer ranging between about one and about 100; and $A^2$ is the same as A in Formula II and IIa. Block copolymers according to the present invention include copolymers containing molar fractions of alkylene oxide between about 0.1 and about 25%. Other block copolymers according to the present invention contain molar fractions of alkylene oxide between about 0.5 and about 10%. Yet other block copolymers according to the present invention contain molar fractions of alkylene oxide between about 1 and about 5%.

Independent of any particular polymer embodiment, the present invention also provides copolymers with two different repeating units with the structure of Formula I and/or Formula II, wherein the copolymer has a first repeating unit in which $R_2$ is hydrogen, and a second repeating unit in which $R_2$ is an alkyl group containing from one to six carbon atoms. Copolymers with repeating units in which $R_2$ is alkyl are referred to as N-substituted copolymers and are prepared from N-substituted monomers by the methods disclosed by U.S. patent application Ser. No. 11/873,979, the disclosure of which is incorporated herein by reference.

N-substituted copolymers according to the present invention include copolymers in which the molar fraction of N-substituted monomer is between about 1 and about 90%. N-substituted copolymers according to the present invention also include copolymers with a molar fraction of N-substituted monomer between about 5 and about 25%. Yet other N-substituted co-polymers according to the present invention include copolymers with a molar fraction of N-sub-stituted monomer between about 7.5 and about 12.5%.

Independent of any particular polymer embodiment, polymers according to the present invention include polymers in which the thermal decomposition temperature is greater than the glass transition temperature or the crystalline melt temperature. Such polymers can be melt-processed and can be shaped into different three-dimensional structures for specific uses by conventional polymer-forming techniques such as extrusion and injection molding. The solvent-casting and compression molding techniques described in earlier patents disclosing polymers polymerized from tyrosine-derived diphenol compounds can also be used for all polymers provided by the present invention, regardless of whether they can be melt-processed.

Therefore, according to another aspect of the present invention, blood-contacting or tissue-implantable medical devices are provided, formed from the polymers of the present invention. Preferably, the devices are formed by thermal fabrication. Such devices include hernia repair devices. Load-bearing medical devices are formed from the first and second polymer embodiments, while medical devices that are not load-bearing may be formed from all four polymer embodiments.

Load-bearing medical devices formed from the first and second polymer embodiments of the present invention include stents for the treatment of a body lumen including, but not limited to, any blood vessels, the esophagus, urinary tract, bile tract, and the ventricles of the central nervous system (brain and spinal cord). Preferred stents are formed from or coated with radio-opaque polymers according to the first and second polymer embodiments of the present invention, so that fluoroscopic imaging can be used to guide positioning of the device. One radio-opaque, bioresorbable stent provided by the present invention is formed from a bioresorbable polymer with sufficient halogen atoms to render the stent inherently visible by X-ray fluoroscopy during stent placement.

Included among the medical devices formed from the polymers of the present invention are embolotherapy products. Embolotherapy products provided by the present invention include particulate formulations of biocompatible, bioresorbable polymers according to all four polymer embodiments of the present invention. Among the embolotherapy products provided by the present invention are embolotherapy products formed from the radio-opaque polymers provided by the present invention that contain a sufficient number of halogen atoms to render the embolotherapy product inherently radio-opaque.

Another specific application for which polymers provided by the present invention are particularly useful is the fabrication of scaffolds for tissue engineering on which isolated cell populations are transplanted to engineer new tissues. The polymers are formed into porous devices as described by Mikos et al., Biomaterials, 14, 323-329 (1993) or Schugens et al., J. Biomed. Mater. Res., 30, 449-462 (1996) or U.S. Pat. No. 6,103,255 to allow for the attachment and growth of cells as described in Bulletin of the Material Research Society, Special Issue on Tissue Engineering (Guest Ed.: Joachim Kohn), 21(11), 22-26 (1996). Thus the present invention also provides tissue scaffolds having a porous structure for the attachment and proliferation of cells either in vitro or in vivo formed from polymers provided by the present invention. Which polymer embodiment disclosed herein should be used to fabricate the scaffold will depend upon the degree of rigidity and rate of resorption required by the intended scaffold use.

Another specific application for which polymers provided by the present invention may be used is the fabrication of implantable drug delivery devices where a pharmaceutically active moiety is admixed within the polymeric matrix for slow release, including devices for ophthalmic drug delivery. The polymers provided by the present invention are combined with a quantity of a biologically or pharmaceutically active compound sufficient to be therapeutically effective as a site-specific or systemic drug delivery system as described by Gutowska et al., J. Biomater. Res., 29, 811-21 (1995) and Hoffman, J. Contr. Rel., 6, 297-305 (1987). Accordingly, the present invention also provides a method for site-specific or systemic drug delivery by implanting in the body of a patient in need thereof an implantable drug delivery device containing a therapeutically effective amount of a biologically or a physiologically active compound in combination with a polymer provided by the present invention.

Independent of any particular polymer embodiment, the polymers provided by the present invention have good filmforming properties. An important phenomena observed for the polymers provided by the present invention having poly (alkylene oxide) block copolymer segments is the temperature dependent phase transition of the polymer gel or the polymer solution in aqueous solvents. As the temperature increases, the gel of the polymers undergo a phase transition to a collapsed state, while polymer solutions precipitate at a certain temperature or within certain temperature ranges. The polymers of the present invention having poly(alkylene oxide) segments, and especially those that undergo a phase transition at about 30 to 40° C. on heating can be used as biomaterials for drug release and clinical implantation materials. Specific applications include films and sheets for the prevention of adhesion and tissue reconstruction, as well as injectable drug delivery systems that exist as a solution at room temperature and that precipitate to form a solid drug release device upon injection into the patient.

Therefore, the present invention also provides sheets or coatings for application to exposed or injured tissues for use as barrier for the prevention of surgical adhesions as described by Urry et al., Mat. Res. Soc. Symp. Proc., 292, 253-64 (1993), which are formed from the poly(alkylene oxide) block copolymers provided by the present invention. In addition, the present invention also provides a method for preventing the formation of adhesions between injured tissues by inserting as a barrier between the injured tissues a sheet or a coating of the poly(alkylene oxide) block copolymers provided by the present invention.

The poly(alkylene oxide) segments decrease the surface adhesion of the polymers provided by the present invention. As the molar fraction of poly(alkylene oxide) increases, the surface adhesion decreases. Coatings containing polymers with poly(alkylene oxide) segments provided by the present invention may thus be prepared that are resistant to cell attachment and are useful as non-thrombogenic coatings on surfaces in contact with blood. Such polymers also resist bacterial adhesion in this and in other medical applications as well. The present invention therefore also provides blood contacting devices and medical implants having surfaces coated with the poly(alkylene oxide) block copolymers provided by the present invention.

The coated surfaces are preferably polymeric surfaces. Methods provided by the present invention therefore further include implanting in the body of a patient a blood-contacting device or medical implant having a surface coated with a polymer provided by the present invention containing poly (alkylene oxide) block copolymer segments.

By varying the molar fraction of poly(alkylene oxide) segments in the block copolymers provided by the present invention, the hydrophilic/hydrophobic ratios of the polymers can be attenuated to adjust the ability of the polymer coatings to modify cellular behavior. Increasing levels of poly(alkylene oxide) inhibit cellular attachment, migration and proliferation, while increasing the amount of pendent free carboxylic acid groups promotes cellular attachment, migration and proliferation. The present invention therefore also provides methods for regulating cellular attachment, migration and proliferation by contacting living cells, tissues, or biological fluids containing living cells with the polymers provided by the present invention.

Through pendant free carboxylic acid groups, derivatives of biologically and pharmaceutically active compounds, including drugs, can be attached to the polymer backbone by covalent bonds linked to the carboxylic acid pendent chain. This provides for the sustained release of the biologically or pharmaceutically active compound by means of hydrolysis of the covalent bond between the drug and the polymer backbone. The present invention therefore also provides polymers according to the depicted formulas in which $R_4$ is a biologically or pharmaceutically active compound covalently attached to the polymer backbone.

Other features of the present invention will be pointed out in the following description and claims, which disclose the principles of the invention and the best modes which are presently contemplated for carrying them out.

DETAILED DESCRIPTION OF PREFERRED EMBODIMENTS

The present invention provides new monomer compounds having the structure of Formula IV and Formula IVa:

(IV)

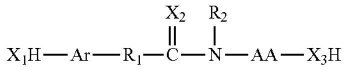

(IVa)

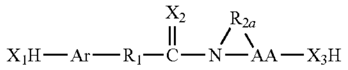

for which the variables are defined as follows:

Ar is a phenyl ring that is unsubstituted or substituted with from one to four substituents independently selected from the group consisting of halogen atoms, halomethyl groups, halomethoxy groups, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from one to six carbon atoms bonded only to N, or $R_{2a}$ is an alkylene group covalently bonded to both the nitrogen atom and AA, so that —N—$R_{2a}$-AA- define a heterocyclic ring;

$R_3$ is selected from the group consisting of hydrogen and alkyl groups containing from one to six carbon atoms;

AA has a pendant $COOR_4$ group in which $R_4$ is selected from the group consisting of hydrogen, alkyl, heteroalkyl and alkylaryl groups containing up to 18 carbon atoms and alkyl-terminated poly(alkylene oxide) groups of molecular weight 100 to 10,000; and AA and $X_3H$ of Formula IV are selected so that ($R_2$—HN—)AA-$X_3H$ define an amino acid and AA and $X_3H$ of Formula IVa are selected so that

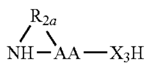

define an $X_3H$— substituted amino acid. According to one embodiment:

defines a proline ring.

Analogs of Formula (IV) and Formula (IVa) have been disclosed in PCT Application Publication No. WO 2010/

033640 by the present applicant, which is hereby incorporated by reference in its entirety.

Thus, in one aspect the present invention provides a biocompatible polymer having the structure of Formula I or Formula Ia:

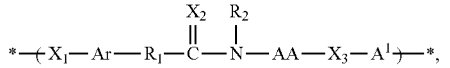

(I)

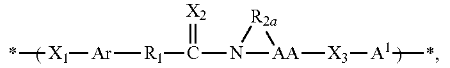

(Ia)

for which the variables are defined as follows:

Ar is a phenyl ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA- define a heterocyclic ring;

$R_3$ is selected from the group consisting of hydrogen and alkyl groups containing from 1 to 30 carbon atoms;

AA has a pendant $COOR_4$ group in which $R_4$ is selected from the group consisting of hydrogen, alkyl, heteroalkyl and alkylaryl groups containing up to 30 carbon atoms and alkyl-terminated poly(alkylene oxide) groups of molecular weight 100 to 10,000;

AA and $X_3H$ of Formula I are selected so that ($R_2$—HN—) AA-$X_3H$ defines an —$X_3H$ substituted amino acid and AA and $X_3H$ of Formula Ia are selected so that

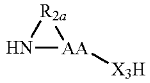

defines an $X_3H$— substituted amino acid;

$A^1$ at each occurrence is independently selected from:

a bond,

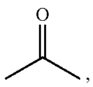, 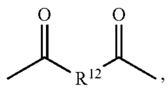, 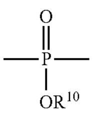, 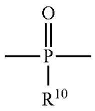, and 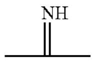;

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl;

wherein said polymer has a glass transition temperature or crystalline melting temperature greater than 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of at least about 3 mg/mL.

In one embodiment of this aspect, the present invention provides a biocompatible polymer comprising repeating units of Formula (I) or (Ia) wherein AA and $X_3$ are selected so that

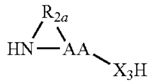

defines an amino acid selected from the group consisting of hydroxy-tryptophan, mercapto-tryptophan, hydroxy-proline and mercapto-proline.

In another embodiment of this aspect, the present invention provides a biocompatible polymer comprising Formula (I) or (Ia) repeating units, wherein said Formula (I) and Formula (Ia) variables are selected to provide a polymer with an equilibrium water content in phosphate buffered saline (PBS) (0.1 M, pH 7.4) at 37° C. of less than about 20 wt %.

In another aspect, the present invention provides a biocompatible polymer comprising repeating units having structures independently selected from Formula (I) and Formula (Ia):

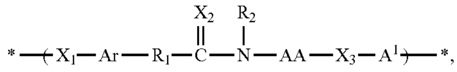

(I)

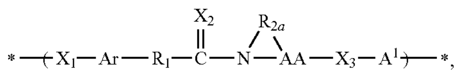

(Ia)

for which the variables are defined as follows:

Ar is a phenyl ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA- define a heterocyclic ring;

$R_3$ is selected from the group consisting of hydrogen and alkyl groups containing from 1 to 30 carbon atoms;

AA has a pendant $COOR_4$ group in which $R_4$ is selected from the group consist-ing of hydrogen, alkyl, heteroalkyl and alkylaryl groups containing up to 30 carbon atoms and alkyl-terminated poly(alkylene oxide) groups of molecular weight 100 to 10,000;

AA and $X_3H$ of Formula (I) are selected so that ($R_2$—HN—)AA-$X_3H$ defines an —$X_3H$ substituted amino acid and AA and $X_3H$ of Formula (Ia) are selected so that

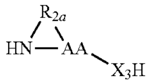

defines an $X_3H$— substituted amino acid;

$A^1$ at each occurrence is independently selected from:

a bond,

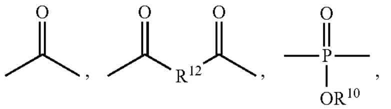

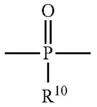, and 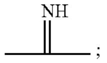;

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl;

wherein said polymer has a glass transition temperature or crystalline melting temperature greater than 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of less than about 3 mg/mL.

In one embodiment of this aspect, the present invention provides a biocompatible polymer comprising repeating unit of Formula (I) or (Ia), wherein AA and $X_3$ are selected so that

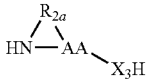

defines an amino acid selected from the group consisting of mercapto-phenylalanine, thryronine and thyroxine.

In an embodiment of this aspect the present invention provides biocompatible polymers comprising repeating units of Formula (I) or (Ia) where the Formula (I) and Formula (Ia) variables are selected to provide a polymer with an equilibrium water content in phosphate buffered saline (PBS) (0.1 M, pH 7.4) at 37° C. of less than about 20 wt %.

In another aspect, the present invention provides a biocompatible polymer comprising repeating units having structures independently selected from Formula (I) and Formula (Ia):

(I)

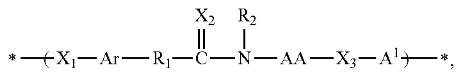

(Ia)

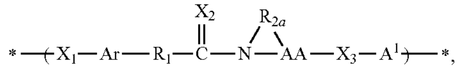

for which the variables are defined as follows:

Ar is a phenyl ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA-define a heterocyclic ring;

$R_3$ is selected from the group consisting of hydrogen and alkyl groups containing from 1 to 30 carbon atoms;

AA has a pendant $COOR_4$ group in which $R_4$ is selected from the group consist-ing of hydrogen, alkyl, heteroalkyl and alkylaryl groups containing up to 30 carbon atoms and alkyl-terminated poly(alkylene oxide) groups of molecular weight 100 to 10,000;

AA and $X_3H$ of Formula (I) are selected so that ($R_2$—HN—)AA-$X_3H$ defines an —$X_3H$ substituted amino acid and AA and $X_3H$ of Formula (Ia) are selected so that

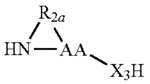

defines an $X_3H$— substituted amino acid;

$A^1$ at each occurrence is independently selected from:

a bond,

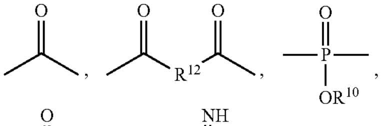

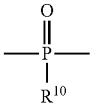, and 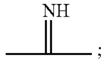;

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl;

wherein said polymer has a glass transition temperature or crystalline melting temperature less than about 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. greater than about 3 mg/mL.

In one embodiment of this aspect, the present invention provides a biocompatible polymer comprising repeating units of Formula (I) or (Ia), wherein ($R_2$—HN—)AA-$X_3H$ defines an amino acid selected from the group consisting of hydroxy-leucine, mercapto-leucine, hydroxy-isoleucine, mercapto-isoleucine and mercapto-valine.

In an embodiment of this aspect, the present invention provides a biocompatible polymer comprising repeating units of Formula (I) or (Ia), wherein said Formula (I) and Formula (Ia) variables are selected to provide a polymer with an equilibrium water content in phosphate buffered saline (PBS) (0.1 M, pH 7.4) at 37° C. of greater than about 10 wt %.

In another aspect, the present invention provides a biocompatible polymer comprising repeating units having a structure selected from Formula (I) and Formula (Ia):

(I)

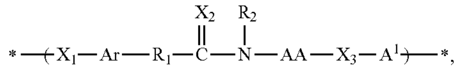

(Ia)

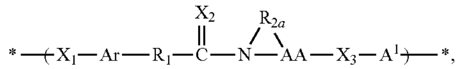

for which the variables are defined as follows:

Ar is a phenyl ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA-define a heterocyclic ring;

$R_3$ is selected from the group consisting of hydrogen and alkyl groups containing from 1 to 30 carbon atoms;

AA has a pendant $COOR_4$ group in which $R_4$ is selected from the group consist-ing of hydrogen, alkyl, heteroalkyl and alkylaryl groups containing up to 30 carbon atoms and alkyl-terminated poly(alkylene oxide) groups of molecular weight 100 to 10,000;

A and $X_3$H of Formula (I) are selected so that ($R_2$—HN—)AA-$X_3$H defines an —$X_3$H substituted amino acid and AA and $X_3$H of Formula (Ia) are selected so that

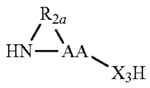

defines an $X_3$H— substituted amino acid;

$A^1$ at each occurrence is independently selected from:

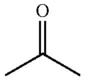, 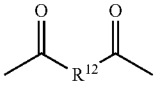, 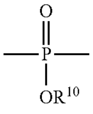, 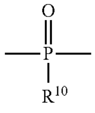, and 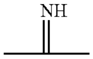;

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl;

wherein said polymer has a glass transition temperature or crystalline melting temperature less than about 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of less than about 3 mg/mL.

In one embodiment of this aspect, the present invention provides a biocompatible polymer comprising repeating units of Formula (I) or (Ia), wherein AA and $X_3$H of Formula (I) are selected so that ($R_2$—HN—)AA-$X_3$H defines an amino acid selected from the group consisting of cysteine, threonine, serine, lysine and mercapto-alanine.

In an embodiment of this aspect, the present invention provides a biocompatible polymer comprising repeating units of Formula (I) or (Ia), wherein said Formula (I) and Formula (Ia) variables are selected to provide a polymer with an equilibrium water content in phosphate buffered saline (PBS) (0.1 M, pH 7.4) at 37° C. of greater than about 10 wt %.

In one embodiment according to any of the above aspects, the present invention provides a biocompatible polymer comprising repeating units of Formula (I) or (Ia), wherein AA and $X_3$H of Formula (I) are selected so that ($R_2$—HN—)AA-$X_3$H defines an alpha amino acid, and wherein AA and $X_3$H of Formula (Ia) are selected so that

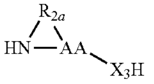

defines an alpha-amino acid.

In another embodiment according to any of the above aspects, the present invention provides a biocompatible polymer comprising repeating units of Formula (I) or (Ia), wherein said alpha amino acid is a naturally-occurring amino acid.

In another embodiment according to any of the above aspects, the present invention provides a biocompatible polymer comprising repeating units of Formula (I) or (Ia), wherein said alpha amino acid is an essential amino acid.

In another embodiment according to any of the above aspects, the present invention provides a biocompatible polymer comprising two different repeating units having the structures of Formula (I) and Formula (Ia), wherein said polymer comprises a first repeating unit in which $R_4$ is hydrogen, so that $COOR_4$ is a pendant free carboxylic acid group, and a second repeating unit in which $R_4$ is an alkyl group containing up to 30 carbon atoms so that $COOR_4$ is a pendant carboxylate group.

In another embodiment according to any of the above aspects, the present invention provides a biocompatible polymer comprising repeating units of Formula (I) or (Ia), as described above, wherein between about 1 and about 50% of the AA groups have pendant free carboxylic acid groups.

In another embodiment according to any of the above aspects, the present invention provides a biocompatible polymer comprising repeating units of Formula (I) or (Ia), wherein at least 50% of the Ar groups are substituted with two to four atoms selected from the group consisting of iodine atoms and bromine atoms.

In another embodiment according to any of the above aspects, the present invention provides a biocompatible polymer comprising repeating units of Formula (I) or (Ia), wherein $R_1$ is —O—$CH_2$—.

In another embodiment according to any of the above aspects, the present invention provides a biocompatible polymer comprising repeating units of Formula (I) or (Ia), wherein $X_1$, $X_2$ and $X_3$ are all oxygen.

In another embodiment according to any of the above aspects, the present invention provides a biocompatible polymer comprising repeating units of Formula (I) or (Ia), characterized by being a polycarbonate, polyester, poly(phosphazine), poly(phosphoester), poly(imino-carbonate), polyether, poly-urethane, poly(carbamate), poly(thiocarbonate), poly(carbonodithionate) or poly(thiocarbamate).

In another embodiment according to any of the above aspects, the present invention provides a biocompatible polymer comprising repeating units of Formula (I) or (Ia), characterized by being a polyalkylene oxide block copolymer.

In another embodiment according to any of the above aspects, the present invention provides a biocompatible polymer comprising repeating units of Formula (I) or (Ia) wherein $R_1$ is —O—$CH_2$—, $X_1$, $X_2$ and $X_3$ are 0 and Ar is a phenyl group optionally substituted with two to four atoms selected from the group consisting of iodine atoms and bromine atoms.

In an embodiment according to any of the above aspects, the present invention provides a biocompatible polymer comprising repeating units of Formula (I) or (Ia), further comprising polyalkylene oxide block repeating units having structures according to Formula (III):

$$-\!\!\left(B-A^2\right)\!\!- \quad \text{(III)}$$

wherein B is —O—$((CHR^6)_p$—$O)_q$—; each $R^6$ is independently H or $C_1$ to $C_3$ alkyl; p is an integer in the range of one to about 4; q is an integer in the range of one to about 100; and $A^2$ is selected from the group consisting of:

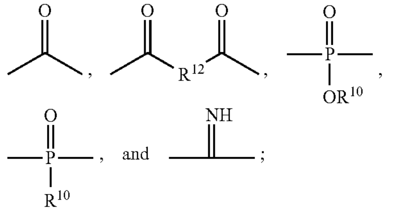

wherein $R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl.

In another embodiment according to any of the above aspects, the present invention provides a biocompatible polymer comprising repeating units of Formula (I) or (Ia), and a third repeating unit of Formula (III), wherein $R^6$ is —$CH_2$—.

The monomer compounds are polymerized to form tissue compatible bioerodable polymers for medical uses. The diphenol monomers can be used in any conventional polymerization process using diphenol monomers, including those processes that synthesize polymers traditionally considered hydrolytically stable and non-biodegradable.

This includes the above-depicted polyesters, polycarbonates, polyimino-carbonates, polyarylates, polyurethanes, polyphosphazine polyphosphonates and polyethers, as well as random block copolymers of these polymers with poly (alkylene oxides) as described in U.S. Pat. No. 5,658,995, the disclosure of which is incorporated herein by reference.

It is also understood that the presentation of the various polymer formulae that polymer structures represented may include homopolymers and heteropolymers, which include stereoisomers. Homopolymer is used herein to designate a polymer comprised of all the same type of monomers. Heteropolymer is used herein to designate a polymer comprised of two or more different types of monomer, which is also called a co-polymer. A heteropolymer or co-polymer may be of a kind known as block, random and alternating. Further with respect to the presentation of the various polymer formulae, products according to embodiments of the present invention may be comprised of a homopolymer, heteropolymer and/or a blend of such polymers.

Polyiminocarbonates are synthesized from diphenol monomers via one of the appropriate methods disclosed by U.S. Pat. No. 4,980,449, the disclosure of which is incorporated by reference. According to one method, part of the diphenol compound is converted to the appropriate dicyanate, then, equimolar quantities of the diphenol compound and the dicyanate are polymerized in the presence of a strong base catalyst such as a metal alkoxide or metal hydroxide.

The monomers compounds of Formula I may also be reacted with phosgene to form polycarbonates with —O—C(═O)—O— linkages. The method is essentially the conventional method for polymerizing diols into polycarbonates. Suitable processes, associated catalysts and solvents are known in the art and are taught in Schnell, Chemistry and Physics of Polycarbonates, (Interscience, New York 1964), the teachings of which are also incorporated herein by reference.

Other methods adaptable for use to prepare polycarbonate polymers of the present invention are disclosed in U.S. Pat. Nos. 6,120,491, and 6,475,477 the disclosures of which are incorporated herein by reference. Polycarbonates may also be prepared by dissolving the Formula I monomer in methylene chloride containing 0.1M pyridine or triethylamine. A solution of phosgene in toluene at a concentration between about 10 and about 25 wt %, and preferably about 20 wt %, is added at a constant rate, typically over about two hours, using a syringe pump or other means. The reaction mixture is quenched by stifling with tetrahydrofuran (THF) and water, after which the polymer is isolated by precipitation with isopropanol (IPA). Residual pyridine (if used) is then removed by agitation of a THF polymer solution with a strongly acidic resin, such as AMBERLYST 15.

The monomer compounds of Formula I may also be directly reacted with aliphatic or aromatic dicarboxylic acids in the carbodiimide mediated process disclosed by U.S. Pat. No. 5,216,115 using 4-(dimethylamino)pyridinium-p-toluene sulfonate (DPTS) as a catalyst to form the aliphatic or aromatic poly(ester amides). The disclosure of U.S. Pat. No. 5,216,115 is incorporated by reference. Dicarboxylic acids according to one embodiment of the present invention have the structure of Formula V:

HOOC—$R_5$—COOH (V)

in which, for the aliphatic copolymers, $R_5$ is selected from saturated and unsaturated, substituted and unsubstituted alkyl groups containing up to 18 carbon atoms, and preferably from 2 to 12 carbon atoms, and optionally may also include up to eight N, O, P or S atoms. For the aromatic copolymers, $R_3$ is selected from aryl and alkylaryl groups containing up to 24 carbon atoms and preferably from 13 to 20 carbon atoms, and optionally may also include up to eight N, O, P or S atoms. The N-heteroatoms may be N-substituted to reduce polymer $T_g$ and melt viscosity.

The process forms polymers with —O—C(═O)—$R_5$—C(═O)—O— linkages. $R_5$ may be selected so that the dicarboxylic acids employed as the starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R_5$ of Formula V is —$CH_2$—$CH_2$—C(═O)—, —$CH_2$—$CH_2$—, —CH═CH— and —$CH_2$—C(═O)—, respectively).

Another naturally-occurring aliphatic dicarboxylic acid is adipic acid ($R_5$ is (—$CH_2$—$)_4$), found in beet juice. Still yet another biocompatible aliphatic dicarboxylic acid is sebacic acid ($R_5$ is (—$CH_2$—$)_8$), which has been studied extensively and has been found to be nontoxic as part of the clinical evaluation of poly(bis(p-carboxy-phenoxy)propane-co-sebacic acid anhydride) by Laurencin et al., J. Biomed. Mater. Res., 24, 1463-81 (1990).

Other biocompatible aliphatic dicarboxylic acids include oxalic acid ($R_5$ is a bond), malonic acid ($R_5$ is —$CH_2$—), glutaric acid ($R_5$ is (—$CH_2$—$)_3$), pimelic acid ($R_5$ is (—$CH_2$—$)_5$), suberic acid ($R_5$ is (—$CH_2$—$)_6$) and azelaic acid ($R_5$ is (—$CH_2$—$)_7$). $R_5$ can thus represent (—$CH_2$—$)_Q$, wherein Q is between 0 and 8, inclusive. Among the suitable aromatic dicarboxylic acids are terephthalic acid, isophthalic acid and bis(p-carboxy-phenoxy)alkanes such as bis(p-carboxy-phenoxy)propane.

$R_5$ can also have the structure of Formula VI:

$$—(CH_2—)_aO—[(CH_2—)_aCHR_8—O—]_m(CH_2—)_a \quad (VI)$$

wherein a is from 1 to 3, inclusive, m is from 1 to 500,000, inclusive, and $R_4$ is hydrogen or a lower alkyl group containing from one to four carbon atoms. $R_4$ is preferably hydrogen, a is preferably 1, and m is preferably between about 10 and about 100, and more preferably between about 10 and about 50.

The diacids of Formula VI are formed by the oxidation of poly(alkylene oxides) according to well-known methods. One example of such a compound is biscarboxymethyl poly(ethylene glycol), which is commercially available.

$R_5$ can also have the structure of Formula VII:

$$—R_7—C(═O)—O[(—CH_2)_a—CHR_8—O—]_mC(═O)—R_7 \quad (VII)$$

wherein a, m and $R_8$ and the preferred species thereof are the same as described above with respect to Formula VI. $R_7$ is selected from a bond or straight and branched alkyl and alkylaryl groups containing up to 18 carbon atoms.

The dicarboxylic acids of Formula VII are poly(alkylene oxides) bis-functionalized with dicarboxylic acids having the structure of Formula V wherein $R_5$ is the same as described above for Formula V and preferably contains up to 12 carbon atoms.

The poly(alkylene oxides) of Formula VII that are bis-functionalized with dicarboxylic acid are prepared by the reaction of a non-functionalized poly(alkylene oxide) with an excess of either the dicarboxylic acid (mediated by a coupling agent such as dicyclohexyl carbodiimide), the anhydride (e.g. succinic anhydride) in the presence of pyridine or triethylamine, or a dicarboxylic acid chloride (e.g. adipoyl chloride) in the presence of an acid acceptor like triethylamine.

Polymers prepared from the Formula I monomeric starting materials of the present invention with at least one bromine- or iodine-substituted aromatic ring are radio-opaque, such as the polymers prepared from radiopaque diphenol compounds prepared according to the disclosure of U.S. Pat. No. 6,475,477, as well as the disclosure of co-pending and commonly-owned U.S. patent application Ser. No. 10/592,202, the disclosures of both of which are incorporated herein by reference. The iodinated and brominated diphenol monomers of the present invention can also be employed as radio-opacifying, biocompatible non-toxic additives for other polymeric biomaterials.

Bromine and iodine substituted aromatic monomers of the present invention are prepared by well-known iodination and bromination techniques that can be readily employed by those of ordinary skill in the art guided by the above referenced granted patent and pending application (now published) without undue experimentation. The halogenated aromatic compounds from which the halogenated aromatic monomers the present invention are prepared undergo ortho-directed halogenation. The term, "ortho-directed", is used herein to designate orientation of the halogen atom(s) relative to the phenoxy alcohol group.

Random or block copolymers of the Formula Ia polymers of the present invention with a poly(alkylene oxide) may be prepared according to the method disclosed in U.S. Pat. No. 5,658,995, the disclosure of which is also incorporated by reference. The poly(alkylene oxide) is preferably a poly(ethylene glycol) block/unit typically having a molecular weight of less than about 10,000 per unit. More typically, the poly(ethylene glycol) block/unit has a molecular weight less than about 4000 per unit. The molecular weight is preferably between about 1000 and about 2000 per unit.

The molar fraction of poly(ethylene glycol) units in block copolymers may range from greater than zero to less than 1, and is typically greater than zero up to about 0.5, inclusive. More preferably, the molar fraction is less than about 0.25 and yet more preferably, less than about 0.1. In a more preferred variations, the molar fraction may vary from greater than about 0.001 to about 0.08, and most preferably, between about 0.025 and about 0.035.

Unless otherwise indicated, the molar fractions reported herein are based on the total molar amount of poly(alkylene glycol) and non-glycol units in the polymers Applicants have also recognized that the polymer glass transition temperature increases as the degree of halogenation and the molar fraction of free carboxylic acid units increases. Higher weight percentages of poly(alkylene oxide) are typically used in polymers with higher levels of iodination and/or with higher molar fractions of free carboxylic acid units to maintain the polymer glass transition temperature within a desired range for the end use application. N-alkylation provides an alternative means for lowering the polymer glass transition temperature so that the amount of poly(alkylene oxide) may be lowered or eliminated without adversely affecting the polymer melt properties. The present invention thus places more tools at the disposal of the polymer chemist for fine-tuning the physico-mechanical properties of the inventive polymers.

The Formula Ia polymers having weight-average molecular weights above about 20,000, and preferably above about 80,000, calculated from gel permeation chromatography (GPC) relative to polystyrene standards using tetrahydrofuran (THF) as the eluent without further correction.

The polymers of the present invention are defined as including polymers polymerized from Formula I monomers having pendent free carboxylic acid groups ($R_6$=H). However, it is not possible to polymerize polymers having pendent free carboxylic acid groups from corresponding monomers with pendent free carboxylic acid groups without cross-reaction of the free carboxylic acid group with the co-monomer. Accordingly, polymers in accordance with the present invention having pendent free carboxylic acid groups are prepared from homopolymers and copolymers of benzyl and tert-butyl ester monomers of the present invention having the structure of Formula IV in which $R_8$ is a benzyl or tert-butyl group.

The benzyl ester homopolymers and copolymers may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491, the disclosure of which is incorporated herein by reference.

The tert-butyl ester homopolymers and copolymers may be converted to corresponding free carboxylic acid homopolymers and copolymers through the selective removal of the tert-butyl groups by the acidolyis method disclosed by the above-referenced U.S. patent application Ser. No. 10/592,202, also incorporated herein by reference.

The catalytic hydrogenolysis or acidolysis is necessary because the lability of the polymer backbone prevents the employment of harsher hydrolysis techniques.

Applicants have recognized that the molar fraction of free carboxylic acid units in the polymers of the present invention can be adjusted according to the present invention to likewise adjust the degradation/resorbability of devices made from such polymers. For example, applicants have recognized that while poly(DTE-co-35 mol % DT carbonate), (a tyrosine-derived polycarbonate comprising about 35% free carboxylic acid units) is 90% resorbed in about 15 days, polycarbonates with lower amounts of free carboxylic acid will have desirably longer lifetimes in the body. Furthermore, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are required. In certain embodiments where lifetimes of 6 months or more are required, polymers of the presently preferred ranges of free carboxylic acid units tend to be desirable.

After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer-forming techniques such as extrusion, compression molding, injection molding, solvent casting, spin casting, wet spinning, combinations of two or more thereof, and the like. Shaped articles prepared from the polymers are useful, inter alia, as degradable biomaterials for medical implant applications. Such applications include the use of shaped articles as vascular grafts and stents.

Polymers according to the present invention also include polyethers, polyurethanes, poly(carbamates), poly(thiocarbonates), poly(carbonodithionates) and poly(thiocarbamates), which may be prepared from the diphenol compounds of the present invention in accordance with known methods.

The monomers of Formula are prepared following standard procedures of peptide chemistry such as disclosed in J. P. Greenstein and M. Winitz, Chemistry of the Amino Acids, (John Wiley & Sons, New York 1961) and Bodanszky, Practice of Peptide Synthesis (Springer-Verlag, New York, 1984).

Specifically, the monomers are prepared by coupling an aromatic compound having the structure of formula V:

(V)

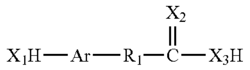

with an amino acid having the structure of Formula VIa or Formula VIb:

(VIa)

$R_2—HN—AA—X_3H$ (VIb)

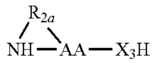

More specifically, the two compounds are coupled by means of carbodiimide-mediated coupling reactions in the presence of hydroxybenzotriazole according to the procedure disclosed in U.S. Pat. Nos. 5,587,507 and 5,670,602, the disclosures of both of which are hereby incorporated by reference. Suitable carbodiimides are disclosed therein. The preferred carbodiimide is 1-ethyl-3-(3-dimethylamino-propyl)carbodiimide hydrochloride (EDCI.HCl). The crude monomers can be recrystallized twice, first from 50% acetic acid and water and then from a 20:20:1 ratio of ethyl acetate, hexane and methanol, or, alternatively, flash chromatography on silica gel is used, employing a 100:2 mixture of methylene chloride:methanol as the mobile phase. More detailed preparation methods are disclosed in PCT Application Publication No. WO 2010/042917, which is hereby incorporated by reference its entirety.

Hydroxyphenyloxy-acetic acid and serine are but two examples of suitable reactants. The other Formula V aromatic compounds and the other Formula VIa and Formula VIb amino acids can be substituted for desaminotyrosine and serine, respectively, in the depicted reaction scheme.

According to one embodiment, $X_1$, $X_2$ and $R_1$ are selected so that Formula V defines a hydroxy-phenyloxyalkanoic or alkenoic acid. Examples of Formula V acids include 4-hydroxy-phenyloxyethanoic acid, 4-hydroxy-phenyloxypropanoic acid, 4-hydroxy-phenyloxybutanoic acid and the like.

According to another embodiment, $R_2$, $R_{2a}$, AA and $X_3$ are selected so that Formula VIa and Formula VIb define an alpha-amino acid. The Formula VIa alpha-amino acid is optionally N-alkyl substituted. In a more specific embodiment, the alpha amino acid is a naturally-occurring amino acid. In an even more specific embodiment, the alpha amino acid is an essential amino acid. Even more specifically, $R_2$, AA and $X_3$ may be selected to define an amino acid selected from cysteine, threonine, serine, lysine, thyronine, thyroxine, hydroxy-proline, mercapto-proline, hydroxy-leucine, mercapto-leucine, hydroxy-isoleucine, mercapto-isoleucine, hydroxy-tryptophan, mercapto-tryptophan, mercapto-alanine, mercapto-valine and mercapto-phenylalanine.

According to another embodiment, the monomer of Formula IV or Formula IVa is an amide dimer of a hydroxyphenyloxy-, hydroxyphenylamino- or hydroxyphenylthio alkanoic or alkenoic acid and an amino acid. Specific examples of this embodiment of Formula IV and IVa monomers include serine-N-[2-(4-hydroxyphenoxy)-1-oxoethyl] ethyl ester, thyroxine-N-[2-(4-hydroxyphenoxy)-1-oxoethyl]ethyl ester, hydroxyproline-N-[2-(4-hydroxyphenoxy)-1-oxoethyl]ethyl ester, and the like.

For purposes of the present invention, a "combination of variables" refers to the combination of $X_1$, $X_2$, $X_3$, $R_1$, $R_2$, $R_{2a}$, $R_3$, $R_4$ and AA variables in Formula I, Formula Ia, Formula II, Formula IIa, Formula IV, Formula IVa, Formula V, Formula VIa and Formula VIb. The present invention provides polymers with combinations of variables and degrees of poly(alkylene oxide) block copolymerization that possess degradation product solubility and the intrinsic physical polymer properties related to suitability for use in load-bearing and non-load-bearing medical implants within one of the four polymer embodiments disclosed herein.

The combination of variables that achieve this result can be readily determined without undue experimentation by one of ordinary skill art guided by the present specification with the objective of achieving a polymer with one of the four combinations of degradation product solubility and intrinsic physical polymer properties described herein. Once appropriate variable combinations are selected, the synthesis of monomers and the polymerization of monomers into polymers is essentially conventional. Thioamide monomers ($X_2$=S) can be prepared using the method described by A. Kjaer (Acta Chemica Scandinavica, 6, 1374-83 (1952)). The amide group in the monomers or polymers can also be converted to thioamide groups using the fluorous analog of the Lawes son's reagent ($f_6$LR) described by Kaleta, et al., Org. Lett., 8(8), 1625-1628 (2006). The second method is preferable, since it allows the formation of the monomer first then allows the conversion of the amide group to the thioamide group. The present invention also includes polymers in which other carboxyl groups, such as the $COOR_4$ group, are replaced with thio groups.

For the conversion of the amide monomers to the corresponding thioamides, the phenolic groups of the monomers are first protected by converting them to the diacetyl esters as shown in the above-referenced U.S. patent application Ser. No. 11/873,979 by treating the monomer with $Ac_2O$/pyridine. The protected monomer is then reacted with $f_6$LR followed by base hydrolysis to the thioamide. The transformation can also be carried out on the polymer using a similar procedure.

The N-substituted monomers and polymers of the present invention ($R_2$=one to six carbon atom alkyl) can be prepared by substituting commercially-available N-substituted starting materials for the starting materials of monomers containing unsubstituted amide groups, or by substituting monomers containing amide groups using non-N-substituted starting materials. Such conversions are described in the above-referenced U.S. patent application Ser. No. 11/873,979, which discloses in one embodiment the preparation of N-substituted alpha-amino acid compounds of Formula IVb from alanine, cysteine, glycine, histidine, isoleucine, phenylalanine, serine, threonine, tryptophan, tyrosine and valine that are subsequently coupled to 4-hydroxy-phenylalkanoic acids to provide N-substituted monomers having the structure of formula IV.

Because the hydroxyphenoxy-, hydroxyphenylamino and hydroxyphenylthio alkanoic acids are non-chiral, unless otherwise indicated the products of this invention are R,S enantiomers. Preferably, however, when a chiral product is desired, the chiral product corresponds to the L-amino acid derivative. Alternatively, chiral products can be obtained via purification techniques which separates enantiomers from an R,S mixture to provide for one or the other stereoisomer. Such techniques are well known in the art.

Polymers according to the present invention may contain a plurality of repeating units containing an N-substituted amide group, wherein the N-substituents and degree of N-substitution are effective to render the polymer processable by a desired processing method. Preferably, the minimum degree of N-substitution is used. This can range from one to three mole percent to render a non-soluble polymer soluble in a given solvent to up to about 25 mole percent to make the same polymer thermally processable, for example, injection moldable. This can be readily determined by one of ordinary skill in the art without undue experimentation. N-methyl substituents are preferred.

The monomer compounds are polymerized to form bioerodable polymers for medical uses. The monomers can be used in any conventional polymerization process using the monomer —$X_1$H and —$X_3$H groups, including those processes that synthesize polymers traditionally considered hydrolytically stable and non-biodegradable. This includes polyesters, polycarbonates, polyiminocarbonates, polyarylates, polyurethanes, poly(urethane carbonates), polyphosphazines, polyphosphoesters, polyethers, poly(carbamates), poly(carbonodithionates), poly(thiocarbonates) and poly (thiocarbamates), as well as random block copolymers of these polymers with poly(alkylene oxides) as described in U.S. Pat. No. 5,658,995, the disclosure of which is incorporated herein by reference.

It is also understood that in the presentation of the various polymer formulae that the polymer structures represented may include homopolymers and heteropolymers, which include stereoisomers. Homopolymer is used herein to designate a polymer comprised of all the same type of monomers. Heteropolymer is used herein to designate a polymer comprised of two or more different types of monomer, which is also called a copolymer. A heteropolymer or co-polymer may be of kinds known as block, random and alternating. Further, with respect to the presentation of the various polymer formulae, products according to embodiments of the present invention may be comprised of a homopolymer, heteropolymer and/or a blend of such polymers and repeating units may be present other than those depicted by Formula! And Formula Ia.

Polyiminocarbonates are synthesized from dihydroxy and diphenol monomers via one of the appropriate methods disclosed by U.S. Pat. No. 4,980,449, the disclosure of which is incorporated by reference. According to one method, part of the dihydroxy or diphenol compound is converted to the appropriate dicyanate, then, equimolar quantities of the dihydroxy or diphenol compound and the dicyanate are polymerized in the presence of a strong base catalyst such as a metal alkoxide or metal hydroxide.

The monomer compounds of formula IV and formula IVa may also be reacted with phosgene to form polycarbonates with —O—C(=O)—O— linkages. The method is essentially the conventional method for polymerizing diols into polycarbonates. Suitable processes, associated catalysts and solvents are known in the art and are taught in Schnell, Chemistry and Physics of Polycarbonates, (Interscience, New York 1964), the teachings of which are also incorporated herein by reference. Because $X_1$ and $X_3$ are independently selected from O, S and $NR_3$, the reaction of the formula IV and formula IVa monomers with phosgene will also produce urethane linkages (—$NR_3$—(C═O)—$NR_3$—), carbono-dithioate linkages (—S—(C═O)—S—), carbamate linkages (—O—(C═O)—$NR_3$—), thio-carbonate linkages (—S—(C═O)—O—) and thio-carbamate linkages (—S—(C═O)—$NR_3$—).

Other methods adaptable for use to prepare the polycarbonate and other phosgene-derived polymers of the present invention are disclosed in U.S. Pat. Nos. 6,120,491, and 6,475,477 the disclosures of which are incorporated by reference. The polycarbonates and other phosgene derivatives may also be prepared by dissolving the Formula IV and/or Formula Iva monomer in methylene chloride containing 0.1M pyridine or triethylamine. A solution of phosgene in toluene at a concentration between about 10 and about 25 wt %, and preferably about 20 wt %, is added at a constant rate, typically over about two hours, using a syringe pump or other means. The reaction mixture is quenched by stifling with tetrahydrofuran (THF) and water, after which the polymer is isolated by precipitation with isopropanol. Residual pyridine (if used) is then removed by agitation of a THF polymer solution with a strongly acidic resin, such as AMBERLYST 15.

The monomer compounds of Formula IV and/or Formula IVa may also be directly reacted with aliphatic or aromatic dicarboxylic acids in the carbodiimide mediated process disclosed by U.S. Pat. No. 5,216,115 using 4-(dimethylamino) pyridinium-p-toluene sulfonate (DPTS) as a catalyst to form the aliphatic or aromatic poly(ester amides) when both $X_3$ groups are O. The disclosure of U.S. Pat. No. 5,216,115 is incorporated by reference. Dicarboxylic acids according to one embodiment of the present invention have the structure of Formula VII:

$$HOOC—R_5—COOH \qquad (VII)$$

in which, for the aliphatic copolymers, $R_5$ is selected from saturated and unsaturated, substituted and unsubstituted alkyl or heteroalkyl groups containing up to 18 carbon atoms, and preferably from 2 to 12 carbon atoms. Heteroalkyl groups contain up to eight N, O, P or S atoms. For aromatic copolymers, $R_5$ is selected from aryl and alkylaryl groups containing up to 24 carbon atoms and preferably from 13 to 20 carbon atoms, and optionally may also include up to eight N, O, P or S atoms. For both aliphatic and aromatic copolymers, N-heteroatoms may be N-substituted to reduce polymer $T_g$ and melt viscosity.

The process forms polymers with —$X_3$—C(═O)—$R_5$—C(═O)—$X_1$— linkages. $R_5$ may be selected so that the dicarboxylic acids employed as the starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R_5$ of formula VII is —$CH_2$—$CH_2$—C(═O)—, —$CH_2$—$CH_2$—, —CH═CH— and —$CH_2$—C(═O)—, respectively).

Another naturally-occurring aliphatic dicarboxylic acid is adipic acid ($R_5$ is (—$CH_2$—$)_4$), found in beet juice. Still yet another biocompatible aliphatic dicarboxylic acid is sebacic acid ($R_5$ is (—$CH_2$—$)_8$), which has been studied extensively and has been found to be nontoxic as part of the clinical evaluation of poly(bis(p-carboxyphenoxy)propane-co-sebacic acid anhydride) by Laurencin et al., J. Biomed. Mater. Res., 24, 1463-81 (1990).

Other biocompatible aliphatic dicarboxylic acids include oxalic acid ($R_5$ is a bond), malonic acid ($R_5$ is —$CH_2$—), glutaric acid ($R_5$ is (—$CH_2$—$)_3$), pimelic acid ($R_5$ is (—$CH_2$—$)_5$), suberic acid ($R_5$ is (—$CH_2$—$)_6$) and azelaic acid ($R_5$ is (—$CH_2$—$)_7$). $R_5$ can thus represent (—$CH_2$—$)_Q$, where Q is between 0 and 8, inclusive. Among the suitable aromatic dicarboxylic acids are terephthalic acid, isophthalic acid and bis(p-carboxy-phenoxy)alkanes such as bis(p-carboxy-phenoxy)propane.

$R_5$ can also have the structure of Formula VIII:

$$—(CH_2—)_aO[(CH_2—)_aCHR_4—O—]_m(CH_2—)_a \qquad (VIII)$$

wherein a is from 1 to 3, inclusive, m is from 1 to 500,000, inclusive, and $R_4$ is hydrogen or a lower alkyl group containing from one to four carbon atoms. $R_4$ is preferably hydrogen, a is preferably 1, and m is preferably between about 10 and about 100, and more preferably between about 10 and about 50.

The diacids of Formula VIII are formed by the oxidation of poly(alkylene oxides) according to well-known methods. One example of such a compound is biscarboxymethyl poly (ethylene glycol), which is commercially available.

$R_5$ can also have the structure of Formula IX:

$$—R_3—C(═O)—O[(—CH_2)_a—CHR_4—O—]_mC(═O)—R_3 \qquad (IX)$$

wherein a, m and $R_4$ and the preferred species thereof are the same as described above with respect to Formula VIII. $R_3$ is selected from a bond or straight and branched alkyl and alkylaryl groups containing up to 18 carbon atoms.

The dicarboxylic acids of Formula IX are poly(alkylene oxides) bis-functionalized with dicarboxylic acids having the structure of Formula VII wherein $R_5$ is the same as described above for Formula VII and preferably contains up to 12 carbon atoms.

The poly(alkylene oxides) of Formula IX that are bis-functionalized with dicarboxylic acids are prepared by the reaction of a non-functionalized poly(alkylene oxide) with an excess of either the dicarboxylic acid (mediated by a coupling agent such as dicyclohexyl carbodiimide), the anhydride (e.g. succinic anhydride) in the presence of pyridine or triethylamine, or a dicarboxylic acid chloride (e.g. adipoyl chloride) in the presence of an acid acceptor like triethylamine.

Polymers prepared from the Formula IV and Formula IVa starting materials of the present invention with at least one bromine- or iodine-substituted aromatic ring are radio-opaque, such as the polymers prepared from radiopaque diphenol compounds prepared according to the disclosure of U.S. Pat. No. 6,475,477, as well as the disclosure of co-pending and commonly-owned U.S. patent application Ser. No. 10/592,202, the disclosures of both of which are incorporated herein by reference. The iodinated and brominated diphenol monomers of the present invention can also be employed as radio-opacifying, biocompatible non-toxic additives for other polymeric biomaterials.

Bromine and iodine substituted aromatic monomers of the present invention are prepared by well-known iodination and bromination techniques that can be readily employed by those of ordinary skill in the art guided by the above referenced granted patent and pending application (now published) without undue experimentation. The halogenated aromatic compounds from which the halogenated aromatic monomers of the present invention are prepared undergo ortho-directed halogenation. The term, "ortho-directed", is used herein to designate orientation of the halogen atom(s) relative to the $X_1$ group of the monomer, or the $X_3$ group if the amino acid has an aromatic ring.

Random or block copolymers of the Formula I, Formula Ia, Formula II and Formula IIa polymers of the present invention with a poly(alkylene oxide) may be prepared according to the method disclosed in U.S. Pat. No. 5,658,995, the disclosure of which is also incorporated by reference. The poly(alkylene oxide) is preferably a poly(ethylene glycol) block/unit typically having a molecular weight of less than about 10,000 per unit. More typically, the poly(ethylene glycol) block/unit has a molecular weight less than about 4000 per unit. The molecular weight is preferably between about 1000 and about 2000 per unit.

The molar fraction of poly(ethylene glycol) units in block copolymers may range from greater than zero to less than 1, and is typically greater than zero up to about 0.5, inclusive. More preferably, the molar fraction is less than about 0.25 and yet more preferably, less than about 0.1. In a more preferred variations, the molar fraction may vary from greater than about 0.001 to about 0.08, and most preferably, between about 0.025 and about 0.035.

Unless otherwise indicated, the molar fractions reported herein are based on the total molar amount of poly(alkylene glycol) and non-glycol units in the polymers The polymer glass transition temperature increases as the degree of halogenation and the molar fraction of free carboxylic acid units increase. Higher weight percentages of poly(alkylene oxide) are typically used in polymers with higher levels of iodination or with higher molar fractions of free carboxylic acid units to maintain the polymer glass transition temperature within the desired range for the end use application. N-alkylation provides an alternative means for lowering the polymer glass transition temperature so that the amount of poly(alkylene oxide) may be lowered or eliminated without adversely affecting the polymer melt properties.

The Formula I, Formula Ia, Formula II and Formula IIa polymers have weight-average molecular weights above about 20,000, preferably above 40,000 and more preferably above about 80,000, calculated from gel permeation chromatography (GPC) relative to polystyrene standards using tetrahydrofuran (THF) as the eluent without further correction. Stated another way, the polymers preferably have between about 30 and 50 of the repeating units depicted in Formula I, Formula Ia, Formula II and Formula IIa.

The polymers of the present invention are defined as including polymers polymerized from formula IV and formula IVa monomers having pendent free carboxylic acid groups ($R_4$=H). However, it is not possible to polymerize polymers having pendent free carboxylic acid groups from corresponding monomers with pendent free carboxylic acid groups without cross-reaction of the free carboxylic acid group with the co-monomer. Accordingly, polymers in accordance with the present invention having pendent free carboxylic acid groups are prepared from homopolymers and copolymers of benzyl and tert-butyl ester monomers of the present invention having the structure of formula IV or formula IVa in which $R_4$ is a benzyl or tert-butyl group.

The benzyl ester homopolymers and copolymers may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491, the disclosure of which is incorporated herein by reference. The tert-butyl ester homopolymers and copolymers may be converted to corresponding free carboxylic acid homopolymers and copolymers through the selective removal of the tert-butyl groups by the acidolyis method disclosed by U.S. application Ser. No. 10/592,202, also incorporated herein by reference. The catalytic hydrogenolysis or acidolysis is necessary because the lability of the polymer backbone prevents the employment of harsher hydrolysis techniques.

The molar fraction of free carboxylic acid units in the polymers of the present invention can be adjusted according to the present invention to modify the degradation of devices made from such polymers. For example, polymers with lower amounts of free carboxylic acid will have longer lifetimes in the body. Further, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are required.

After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer thermo-forming techniques such as extrusion and injection molding when the degradation temperature of the polymer is above the glass transition or crystalline melt temperature, or conventional non-thermal techniques can be used, such as compression molding, injection molding, solvent casting, spin casting, wet spinning. Combinations of two or more methods can be used. Shaped articles prepared from the polymers are useful, inter alia, as degradable biomaterials for medical implant applications.

In one embodiment, the medical device is a stent. It is contemplated that a stent may comprise many different types of forms. For instance, the stent may be an expandable stent. In another embodiment, the stent may be configured to have the form of a sheet stent, a braided stent, a self-expanding stent, a woven stent, a deformable stent, or a slide-and-lock stent. Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms.

In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like. Further, stents may be comprised of at least one fiber material, curable material, laminated material, and/or woven material. The medical device may also be a stent graft or a device used in embolotherapy.

Details of stent products and fabrication in which the polymers of the present invention may be employed are disclosed in co-pending and commonly-owned U.S. patent application Ser. No. 10/952,202 filed Sep. 27, 2004, the disclosure of which is incorporated by reference. Stents are preferably fabricated from the radiopaque polymers of the present invention, to permit fluoroscopic positioning of the device.

The highly beneficial combination of properties associated with the polymers provided by the present invention means these polymers are well-suited for use in producing a variety of resorbable medical devices besides stents, especially implantable medical devices that are preferably radiopaque, biocompatible, and have various times of bioresorption. Polymers are provided that are biocompatible for their intended end use and degrade under physiological conditions into degradation products that are also non-toxic in the intended end use of the polymer.

For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that the resorbable polymers of the present invention are well-suited for use in producing a variety of coatings for medical devices, especially implantable medical devices.

Further, in some preferred embodiments, the present polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other resorbable devices that can be advantageously formed from the polymers of the present invention, include devices for use in tissue engineering. Examples of suitable resorbable devices include tissue engineering scaffolds and grafts (such as vascular grafts, grafts or implants used in nerve regeneration). The present resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various resorbable devices useful in dental applications may advantageously be formed according to embodiments of the present invention. For example devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

The polymers of the present invention are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which the polymers of the present invention may be employed are disclosed in co-pending and commonly-owned U.S. patent application Ser. No. 10/952,274 filed Sep. 27, 2004, the disclosure of which is incorporated by reference. Embolotherapy treatment methods are by their very nature local rather than systemic and the products are preferably fabricated from the radiopaque polymers of the present invention, to permit fluoroscopic monitoring of delivery and treatment.

The present polymers are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer of the present invention. Controlled therapeutic agent delivery systems may also be prepared by direct application of the therapeutic agent to the surface of an implantable medical device such as a bioresorbable stent device (comprised of at least one of the present polymers) without the use of these polymers as a coating, or by use of other polymers or substances for the coating.

When $R_4$ is hydrogen, the $COOR_4$ pendant groups of the polymers of the present invention may also be derivatized by the covalent attachment of a therapeutic agent. Depending upon the moieties present on the underivatized therapeutic agent, the covalent bond may be an amide bond or an ester bond. Typically, the therapeutic agent is derivatized at a primary or secondary amine, hydroxyl, ketone, aldehyde or carboxylic acid group. Chemical attachment procedures are described by U.S. Pat. Nos. 5,219,564 and 5,660,822; Nathan et al., Bio. Cong. Chem., 4, 54-62 (1993) and Nathan, Macromol., 25, 4476 (1992), the disclosures of which are incorporated by reference.

The therapeutic agent may first be covalently attached to a monomer, which is then polymerized, or the polymerization may be performed first, followed by covalent attachment of the therapeutic agent. Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymers of the present invention using conventional techniques well-known to those of ordinary skill in the art.

For this therapeutic agent delivery embodiment, it is not essential that the polymer have pendent groups for covalent attachment of the therapeutic agent.

The polymer compositions of the present invention containing therapeutic agents, regardless of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

Implantable medical devices may thus be fabricated that also serve to deliver a therapeutic agent to the site of implantation by being fabricated from or coated with the therapeutic agent delivery system of the present invention in which a polymer of the present invention has a therapeutic agent physically admixed therein or covalently bonded thereto, such as a drug-eluting stent. Embolotherapeutic particles may also be fabricated for delivery of a therapeutic agent.

Examples of biologically or pharmaceutically active therapeutic agents that may be covalently attached to the polymers of the present invention include acyclovir, cephradine, procaine, ephedrine, adriamycin, daunomycin, plumbagin, atropine, quinine, digoxin, quinidine, biologically active peptides, chlorin $e_6$, cephradine, cephalothin, proline and proline analogs such as cis-hydroxy-L-proline, malphalen, penicillin V and other antibiotics, aspirin and other non-steroidal anti-inflammatories, nicotinic acid, chemodeoxycholic acid, chlorambucil, anti-tumor and anti-proliferative agents, including anti-proliferative agents that prevent restenosis, hormones such as estrogen, and the like. Biologically active compounds, for the purposes of the present invention, are additionally defined as including cell attachment mediators, biologically active ligands, and the like.

The invention described herein also includes various pharmaceutical dosage forms containing the polymer-therapeutic agent combinations of the present invention. The combination may be a bulk matrix for implantation or fine particles for administration by traditional means, in which case the dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

The dosage forms may include one or more pharmaceutically acceptable carriers. Such materials are non-toxic to recipients at the dosages and concentrations employed, and include diluents, solubilizers, lubricants, suspending agents, encapsulating materials, penetration enhancers, solvents, emollients, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin, or immunoglobulins, other hydrophilic polymers such as poly(vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counter-ions such as sodium and/or nonionic surfactants such as tween, pluronics or PEG.

Therapeutic agents to be incorporated in the polymer conjugates and physical admixtures of the invention may be provided in a physiologically acceptable carrier, excipient stabilizer, etc., and may be provided in sustained release or timed release formulations supplemental to the polymeric formulation prepared in this invention. Liquid carriers and diluents for aqueous dispersions are also suitable for use with the polymer conjugates and physical admixtures.

Subjects in need of treatment, typically mammalian, using the polymer-therapeutic agent combinations of this invention, can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-therapeutic agent combinations of this invention may be prepared for storage under conditions suitable for the preservation of therapeutic agent activity as well as maintaining the integrity of the polymers, and are typically suitable for storage at ambient or refrigerated temperatures.

Depending upon the particular compound selected, transdermal delivery may be an option, providing a relatively steady delivery of the drug, which is preferred in some circumstances. Transdermal delivery typically involves the use of a compound in solution, with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The polymer-drug formulations of this invention may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally or via inhalation. Therapeutic agent toxicity could thus be reduced by selective delivery to the affected site. For example if the therapeutic agent is liposome encapsulated, and is injected intravenously, the liposomes used are taken up by vascular cells and locally high concentrations of the therapeutic agent could be released over time within the blood vessel wall, resulting in improved action of the therapeutic agent. The liposome encapsulated therapeutic agents are preferably administered parenterally, and particularly, by intravenous injection.

Liposomes may be targeted to a particular site for release of the therapeutic agent. This would obviate excessive dosages that are often necessary to provide a therapeutically useful dosage of a therapeutic agent at the site of activity, and consequently, the toxicity and side effects associated with higher dosages.

Therapeutic agents incorporated into the polymers of this invention may desirably further incorporate agents to facilitate their delivery systemically to the desired target, as long as the delivery agent meets the same eligibility criteria as the therapeutic agents described above. The active therapeutic agents to be delivered may in this fashion be incorporated with antibodies, antibody fragments, growth factors, hormones, or other targeting moieties, to which the therapeutic agent molecules are coupled.

The polymer-therapeutic agent combinations of this invention may also be formed into shaped articles, such as valves, stents, tubing, prostheses, and the like. Cardiovascular stents may be combined with therapeutic agents that prevent restenosis. Implantable medical devices may be combined with therapeutic agents that prevent infection.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate from the formulations of this invention are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods of this invention, the polymer-therapeutic agent combinations may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

A major advantage of using the radiopaque, bioresorbable polymers of the instant invention in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and were used as received, unless otherwise indicated.

EXAMPLES

The ethyl esters of the amino acids were prepared using by reaction with ethanol and thionyl chloride as described in a literature procedure (Bodanszky, Practice of Peptide Synthesis (Springer-Verlag, New York, 1984). The products were characterized by HPLC, 1H NMR, and elemental analysis and melting point.

Example 1

Synthesis of L-serine-N-[2-(4-hydroxyphenoxy)-1-oxoethyl]ethyl ester

To a single-neck 500 mL round-bottom flask equipped with an addition funnel and a magnetic stirrer is added 16.8 g (0.100 mol) of (4-hydroxyphenoxy)acetic acid (HPA), serine-ethyl ester hydrochloride (10.7 g, 63.2 mmol), hydroxybenzotriazole hydrate (0.81 g, 6.0 mmol), and tetrahydrofuran (50 mL). The flask is cooled in an ice-water bath and triethylamine (8.85 mL, 63.4 mmol) is added drop wise over a period of 10 minutes and the reaction mixture is stirred for 30 more minutes and then 1-ethyl-3-[3-(dimethylamino)propyl]carbodiimide hydro-chloride (12 g, 50 mmol) is added and stirred at ice-water bath temperature for 1 hour.

The reaction mixture is further stirred at room temperature for 4 hours. Distilled water (150 mL) was added to the reaction flask and mixture is stirred for 30 minutes after which, mixture is allowed to stand until the layers separated. The top layer is removed and discarded. The bottom layer is dissolved in ethyl acetate (200 mL). The solution is washed twice with 0.4 M hydrochloric acid solution (100 mL), twice with 0.5 M sodium bicarbonate solution (100 mL), and twice with 20% sodium chloride solution (100 mL). After drying over anhydrous magnesium sulfate and stirring with 100-mesh activated carbon, the solution is filtered until clear. Solvent is removed by rotary evaporation and the monomer is dried under vacuum. The syrupy product obtained is stirred with hexane (100 mL) for 6 h and the product is obtained as white powder. The resulting monomers are characterized by elemental analysis, $^{1}H$ NMR spectroscopy and HPLC

Examples 2 and 3

Synthesis of Other Amino Acid Ethyl Esters

Using the procedure of Example 1, ethyl esters of trans-hydroxyproline and threonine are coupled to (4-hydroxyphenoxy)acetic acid (HPA). The resulting monomers are characterized as in Example 1 by elemental analysis, $^{1}H$ NMR spectroscopy and HPLC.

Examples 4 and 5

Synthesis of Iodinated HPA—Amino Acid Ethyl Esters

Using the procedure of Example 1, thyronine ethyl ester and 5-hydroxytryptophan ethyl esters are coupled with diiodo-HPA {3-(3,5-diiodo-4-hydroxyphenoxy)acetic acid} to get the corresponding diiodinated monomers. The monomers are also characterized as in Examples 1-3.

Example 6

Polymerization of Thyronine-N-[2-(3,5-diiodo-4-hydroxyphenoxy)-1-oxoethyl]Ethyl Ester Using Phosgene In a 100 mL round-bottomed flask equipped with a magnetic stirrer, syringe pump, are placed 2.1 mmol diiodo-(4- hydroxyphenoxy)-1-oxoethyl thyronine ethyl ester, 15 mL methylene chloride, and 0.66 g (8.3 mmol) pyridine), The resulting solution is stirred and to the stirred solution is added 0.25 gram of triphosgene dissolved in 1 mL methylene chloride over a period of 3 h using a syringe pump. The product is isolated by precipitation with 2-propanol. The product is dried in vacuum oven at 40° C. and characterized by GPC, DSC and by $^1$H NMR spectroscopy.

What is claimed is:

1. A polymer comprising repeating units having structures independently selected from Formula (I) and Formula (Ia):

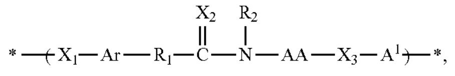

(I)

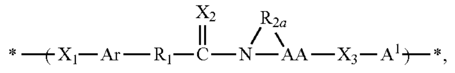

(Ia)

for which the variables are defined as follows:

Ar is a phenylene ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA- define a heterocyclic ring;

$R_3$ is selected from the group consisting of hydrogen and alkyl groups containing from 1 to 30 carbon atoms;

AA has a pendant $COOR_4$ group in which $R_4$ is selected from the group consisting of hydrogen, alkyl, heteroalkyl and alkylaryl groups containing up to 30 carbon atoms and alkyl-terminated poly(alkylene oxide) groups of molecular weight 100 to 10,000;

AA and $X_3$H of Formula I are selected so that ($R_2$—HN—) AA-$X_3$H defines an —$X_3$H substituted amino acid and AA and $X_3$H of Formula Ia are selected so that

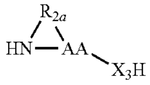

defines an $X_3$H— substituted amino acid;

$A^1$ at each occurrence is independently selected from:

a bond,

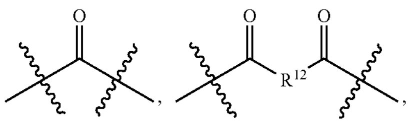

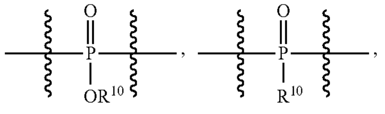

and

-continued

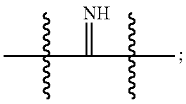

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkylene, alkenylene or alkynylene, $C_1$-$C_{30}$ heteroalkylene, heteroalkenylene or heteroalkynylene, $C_5$-$C_{30}$ heteroalkylarylene, heteroalkenylarylene or heteroalkynylarylene, $C_6$-$C_{30}$ alkylarylene, alkenylarylene or alkynylarylene, and $C_5$-$C_{30}$ heteroarylene;

wherein said polymer has a glass transition temperature or crystalline melting temperature greater than 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of at least about 3 mg/mL.

2. The polymer of claim 1, wherein AA and $X_3$ are selected so that

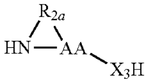

defines an amino acid selected from the group consisting of hydroxy-tryptophan, mercapto-tryptophan, hydroxy-proline and mercapto-proline.

3. A polymer comprising repeating units having structures independently selected from Formula (I) and Formula (Ia):

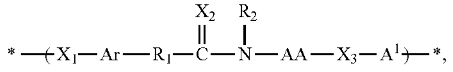

(I)

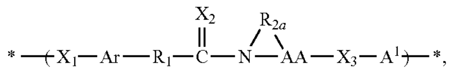

(Ia)

for which the variables are defined as follows:

Ar is a phenylene ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA- define a heterocyclic ring;

$R_3$ is selected from the group consisting of hydrogen and alkyl groups containing from 1 to 30 carbon atoms;

AA has a pendant $COOR_4$ group in which $R_4$ is selected from the group consisting of hydrogen, alkyl, heteroalkyl and alkylaryl groups containing up to 30 carbon atoms and alkyl-terminated poly(alkylene oxide) groups of molecular weight 100 to 10,000;

AA and $X_3H$ of Formula (I) are selected so that ($R_2$—HN—)AA-$X_3H$ defines an —$X_3H$ substituted amino acid and AA and $X_3H$ of Formula (Ia) are selected so that

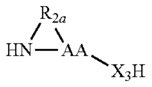

defines an $X_3H$— substituted amino acid;

$A^1$ at each occurrence is independently selected from:

a bond,

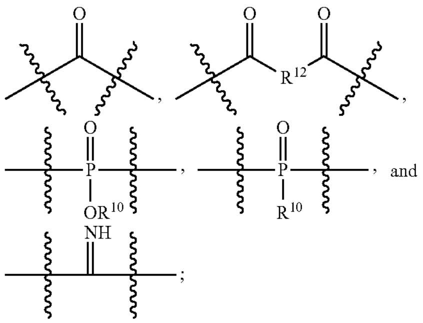

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkylene, alkenylene or alkynylene, $C_1$-$C_{30}$ heteroalkylene, heteroalkenylene or heteroalkynylene, $C_5$-$C_{30}$ heteroalkylarylene, heteroalkenylarylene or heteroalkynylarylene, $C_6$-$C_{30}$ alkylarylene, alkenylarylene or alkynylarylene, and $C_5$-$C_{30}$ heteroarylene;

wherein said polymer has a glass transition temperature or crystalline melting temperature greater than 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of less than about 3 mg/mL.

4. The polymer of claim 3, wherein AA and $X_3$ are selected so that

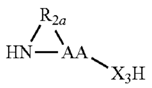

defines an amino acid selected from the group consisting of mercapto-phenylalanine, thyronine and thyroxine.

5. A polymer comprising repeating units having structures independently selected from Formula (I) and Formula (Ia):

(I)

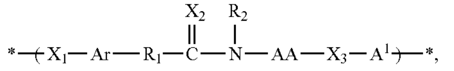

-continued (Ia)

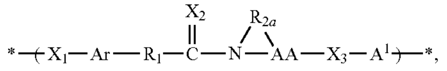

for which the variables are defined as follows:

Ar is a phenylene ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA- define a heterocyclic ring;

$R_3$ is selected from the group consisting of hydrogen and alkyl groups containing from 1 to 30 carbon atoms;

AA has a pendant $COOR_4$ group in which $R_4$ is selected from the group consisting of hydrogen, alkyl, heteroalkyl and alkylaryl groups containing up to 30 carbon atoms and alkyl-terminated poly(alkylene oxide) groups of molecular weight 100 to 10,000;

AA and $X_3H$ of Formula (I) are selected so that ($R_2$—HN—)AA-$X_3H$ defines an —$X_3H$ substituted amino acid and AA and $X_3H$ of Formula (Ia) are selected so that

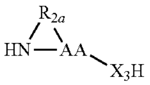

defines an $X_3H$— substituted amino acid;

$A^1$ at each occurrence is independently selected from:

a bond,

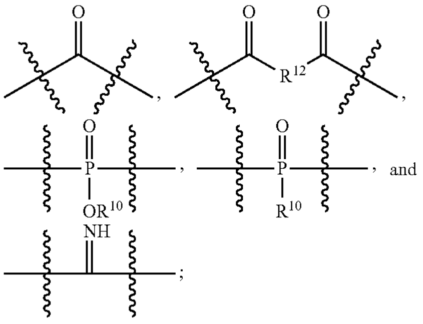

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkylene, alkenylene or alkynylene, $C_1$-$C_{30}$ heteroalkylene, heteroalkenylene or heteroalkynylene, $C_5$-$C_{30}$ heteroalkylarylene, heteroalkenylarylene or heteroalkynylarylene, $C_6$-$C_{30}$ alkylarylene, alkenylarylene or alkynylarylene, and $C_5$-$C_{30}$ heteroarylene;

wherein said polymer has a glass transition temperature or crystalline melting temperature less than about 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. greater than about 3 mg/mL.

6. The polymer of claim 5, wherein ($R_2$—HN—)AA-$X_3$H defines an amino acid selected from the group consisting of hydroxy-leucine, mercapto-leucine, hydroxy-isoleucine, mercapto-isoleucine and mercapto-valine.

7. A polymer comprising repeating units having structures independently selected from Formula (I) and Formula (Ia):

(I)

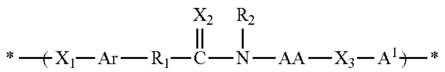

(Ia)

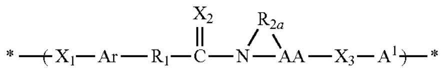

for which the variables are defined as follows:

Ar is a phenylene ring optionally substituted with from one to four substituents independently selected from the group consisting of halogen, halomethyl, halomethoxy, methyl, methoxy, thiomethyl, nitro, sulfoxide and sulfonyl;

$R_1$ is X—$(CH_2)_i$ i is an integer selected from 1 through 4;

X, $X_1$, $X_2$ and $X_3$ are independently selected from the group consisting of O, S and $NR_3$;

$R_2$ is selected from the group consisting of hydrogen and alkyl groups containing from 1 to 30 carbon atoms, or $R_{2a}$ is an alkylene group covalently bonded to both the $NR_2$ nitrogen atom and AA, so that —N—$R_{2a}$-AA-define a heterocyclic ring;

$R_3$ is selected from the group consisting of hydrogen and alkyl groups containing from 1 to 30 carbon atoms;

AA has a pendant $COOR_4$ group in which $R_4$ is selected from the group consist-ing of hydrogen, alkyl, heteroalkyl and alkylaryl groups containing up to 30 carbon atoms and alkyl-terminated poly(alkylene oxide) groups of molecular weight 100 to 10,000;

A and $X_3$H of Formula (I) are selected so that ($R_2$—HN—) AA-$X_3$H defines an —$X_3$H substituted amino acid and AA and $X_3$H of Formula (Ia) are selected so that

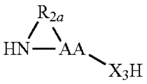

defines an $X_3$H— substituted amino acid;

$A^1$ at each occurrence is independently selected from:

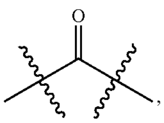, 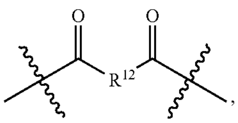, 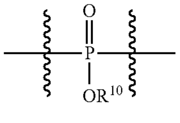, 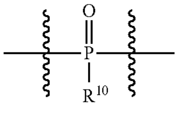, and

-continued

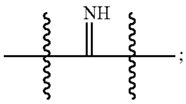;

$R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkylene, alkenylene or alkynylene, $C_1$-$C_{30}$ heteroalkylene, heteroalkenylene or heteroalkynylene, $C_5$-$C_{30}$ heteroalkylarylene, heteroalkenylarylene or heteroalkynylarylene, $C_6$-$C_{30}$ alkylarylene, alkenylarylene or alkynylarylene, and $C_5$-$C_{30}$ heteroarylene;

wherein said polymer has a glass transition temperature or crystalline melting temperature less than about 37° C. when fully hydrated in said PBS solution at 37° C. and said Formula (I) and Formula (Ia) variables are selected so that monomers comprising said Formula (I) and Formula (Ia) repeating units have a solubility in phosphate buffered saline (PBS) (0.1 M, pH 7.4) at 37° C. of less than about 3 mg/mL.

8. The polymer of claim 7, wherein AA and $X_3$H of Formula (I) are selected so that ($R_2$—HN—)AA-$X_3$H defines an amino acid selected from the group consisting of cysteine, threonine, serine, lysine and mercapto-alanine.

9. The polymer of claim 1, wherein said Formula (I) and Formula (Ia) variables are selected to provide a polymer with an equilibrium water content in phosphate buffered saline (PBS) (0.1 M, pH 7.4) at 37° C. of less than about 20 wt %.

10. The polymer of claim 5, wherein said Formula (I) and Formula (Ia) variables are selected to provide a polymer with an equilibrium water content in phosphate buffered saline (PBS) (0.1 M, pH 7.4) at 37° C. of greater than about 10 wt %.

11. The polymer of claim 1, comprising two different repeating units having the structures of Formula (I) and Formula (Ia), wherein said polymer comprises a first repeating unit in which $R_4$ is hydrogen, so that $COOR_4$ is a pendant free carboxylic acid group, and a second repeating unit in which $R_4$ is an alkyl group containing up to 30 carbon atoms so that $COOR_4$ is a pendant carboxylate group.

12. The polymer of claim 11, wherein between about 1% and about 50% of the AA groups have pendant free carboxylic acid groups.

13. The polymer of claim 1, wherein at least 50% of the Ar groups are substituted with two to four atoms selected from the group consisting of iodine atoms and bromine atoms.

14. The polymer of claim 1, wherein $R_1$ is —O—$CH_2$—.

15. The polymer of claim 1, wherein X, $X_1$, $X_2$ and $X_3$ are all oxygen.

16. The polymer of claim 1, characterized by being a polycarbonate, polyester, poly(phosphazine), poly(phosphoester), poly(iminocarbonate), polyether, poly-urethane, poly (carbamate), poly(thiocarbonate), poly(carbonodithionate) or poly(thiocarbamate).

17. The polymer of claim 1, characterized by being a polyalkylene oxide block copolymer.

18. The polymer of claim 1, wherein $R_1$ is —$CH_2$—$CH_2$— or —CH═CH—, $X_1$, $X_2$ and $X_3$ are O, and Ar is a phenylene group optionally substituted with two to four atoms selected from the group consisting of iodine atoms and bromine atoms.

19. The polymer according to claim 1, wherein the second repeating unit is in an amount of at least 10 mol %.

20. The polymer according to claim 1, further comprising polyalkylene oxide block repeating unit having a structure according to Formula III:

$$-(B-A^2)- \quad (III)$$

wherein B is $-O-((CHR^6)_p-O)_q-$; each $R^6$ is independently H or $C_1$ to $C_3$ alkyl; p is an integer in the range of one to about 4; q is an integer in the range of one to about 100; and $A^2$ is selected from the group consisting of:

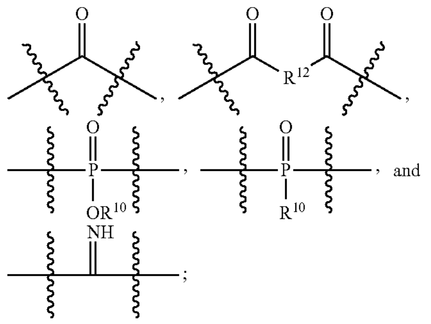

wherein $R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkylene, alkenylene or alkynylene, $C_1$-$C_{30}$ heteroalkylene, heteroalkenylene or heteroalkynylene, $C_5$-$C_{30}$ heteroalkylarylene, heteroalkenylarylene or heteroalkynylarylene, $C_6$-$C_{30}$ alkylarylene, alkenylarylene or alkynylarylene, and $C_5$-$C_{30}$ heteroarylene.

21. The polymer of claim 20, wherein $R^6$ is $-CH_2-$.

22. A drug delivery implant, embolotherapy product, hernia repair mesh, envelope of the implantation of a cardiac device, bridging material, tissue sealant, adhesion prevention material, graft for nerve regeneration, implantable organ support or tissue engineering scaffold comprising the polymer of claim 5, characterized by being a resorbable medical device selected from the group consisting of a vascular graft, a vascular stent, an embolotherapy product, a hernia repair mesh, a gastric lap band, a drug delivery implant, an envelope for the implantation of a cardiac device, a biliary stent, an esophageal stent, a vaginal stent, a lung-trachea/bronchus stent, an orthopedic screw, an orthopedic suture anchor, a tissue engineering scaffold, a graft for nerve re-generation, a suture, a clip, a staple, a barbed suture, a mesh suture and an implantable organ support.

* * * * *